(12) United States Patent
Bern

(10) Patent No.: US 11,128,965 B2
(45) Date of Patent: Sep. 21, 2021

(54) IMPLANTABLE MEDICAL DEVICE COMPRISING A WIRELESS TRANSCUTANEOUS LINK

(71) Applicant: Oticon Medical A/S, Smørum (DK)

(72) Inventor: Bengt Bern, Askim (SE)

(73) Assignee: OTICON MEDICAL A/S, Smørum (DK)

( * ) Notice: Subject to any disclaimer, the term of this patent is extended or adjusted under 35 U.S.C. 154(b) by 186 days.

(21) Appl. No.: 16/100,875

(22) Filed: Aug. 10, 2018

(65) Prior Publication Data

US 2019/0051988 A1    Feb. 14, 2019

(30) Foreign Application Priority Data

Aug. 11, 2017   (EP) ..................................... 17185904

(51) Int. Cl.
*A61B 5/00*      (2006.01)
*H04R 25/00*   (2006.01)
(Continued)

(52) U.S. Cl.
CPC ........... *H04R 25/60* (2013.01); *A61B 5/0031* (2013.01); *A61N 1/0502* (2013.01);
(Continued)

(58) Field of Classification Search
USPC .......................................................... 607/60
See application file for complete search history.

(56) References Cited

U.S. PATENT DOCUMENTS

| 4,696,287 A | 9/1987 | Hortmann et al. |
| 2011/0009924 A1* | 1/2011 | Meskens ............ A61N 1/36038 607/57 |

(Continued)

FOREIGN PATENT DOCUMENTS

| EP | 0 193 145 A2 | 9/1986 |
| EP | 0 193 145 A3 | 9/1986 |

(Continued)

*Primary Examiner* — Nicole F Lavert
(74) *Attorney, Agent, or Firm* — Birch, Stewart, Kolasch & Birch, LLP.

(57) ABSTRACT

According to an embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, and a fixation unit configured to attach the loop structure to a user's body i) proximal to an implantable receiver coil that is configured to be implanted within a body part, and ii) around a body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and when the loop structure is attached using the fixation unit, at least a substantial number of magnetic field lines generated in response to excitation of the transmitter coil passes through the implantable receiver coil.

20 Claims, 7 Drawing Sheets

(51) Int. Cl.
*H01Q 7/06* (2006.01)
*A61N 1/05* (2006.01)
*A61N 1/372* (2006.01)
*H04R 1/10* (2006.01)
*A61N 1/378* (2006.01)
*H01F 38/14* (2006.01)
*A44C 7/00* (2006.01)
*A61M 5/142* (2006.01)
*A61N 1/36* (2006.01)
*A61N 1/375* (2006.01)
*A61M 5/172* (2006.01)
*A61M 60/148* (2021.01)

(52) U.S. Cl.
CPC ......... *A61N 1/0529* (2013.01); *A61N 1/0541* (2013.01); *A61N 1/0563* (2013.01); *A61N 1/0568* (2013.01); *A61N 1/3787* (2013.01); *A61N 1/37217* (2013.01); *H01F 38/14* (2013.01); *H01Q 7/06* (2013.01); *H04R 1/1025* (2013.01); *H04R 25/55* (2013.01); *A44C 7/00* (2013.01); *A61M 5/14276* (2013.01); *A61M 5/1723* (2013.01); *A61M 60/148* (2021.01); *A61M 2202/0413* (2013.01); *A61M 2205/04* (2013.01); *A61M 2205/3303* (2013.01); *A61M 2210/0662* (2013.01); *A61M 2230/005* (2013.01); *A61M 2230/201* (2013.01); *A61N 1/056* (2013.01); *A61N 1/0509* (2013.01); *A61N 1/0543* (2013.01); *A61N 1/0551* (2013.01); *A61N 1/36038* (2017.08); *A61N 1/375* (2013.01); *H04R 2225/57* (2019.05)

(56) References Cited

U.S. PATENT DOCUMENTS

| | | | | |
|---|---|---|---|---|
| 2014/0155950 | A1* | 6/2014 | Hastings | A61N 1/365 607/27 |
| 2015/0209592 | A1* | 7/2015 | Imran | H02J 5/005 607/60 |
| 2016/0344240 | A1* | 11/2016 | Yeh | A61N 1/37229 |

FOREIGN PATENT DOCUMENTS

| | | |
|---|---|---|
| EP | 2 506 922 | 10/2012 |
| WO | WO 2009/056167 A1 | 5/2009 |
| WO | WO 2010/133702 A2 | 11/2010 |
| WO | WO 2010/133702 A3 | 11/2010 |
| WO | WO 2011/068822 A2 | 6/2011 |
| WO | WO 2011/068822 A3 | 6/2011 |

* cited by examiner

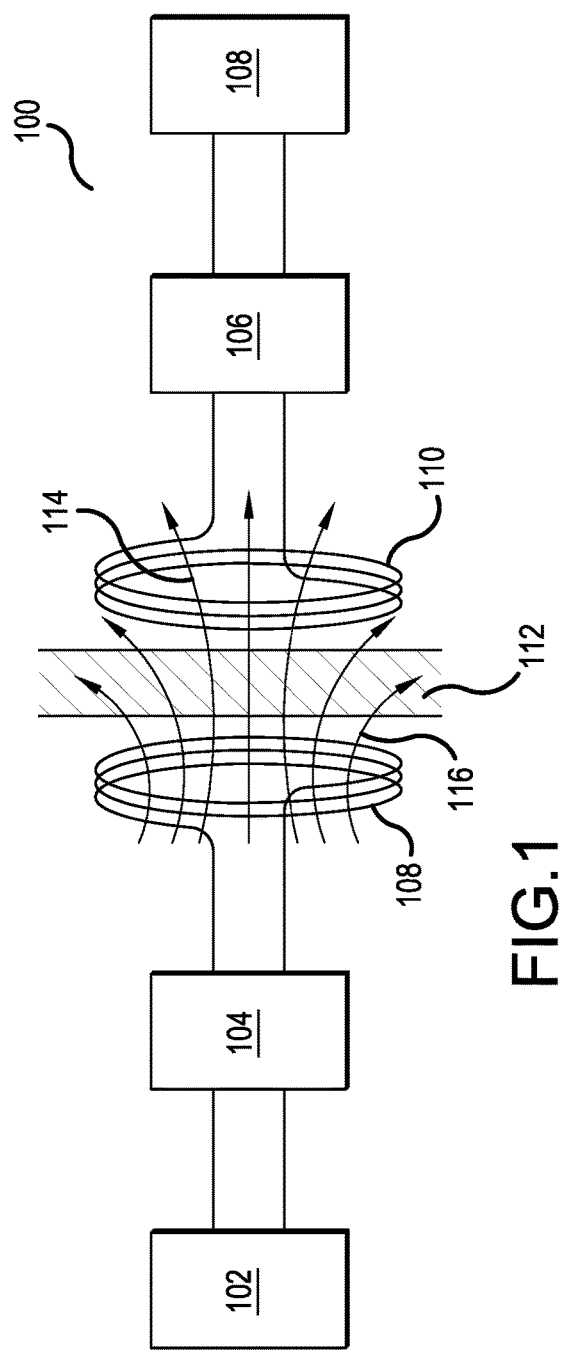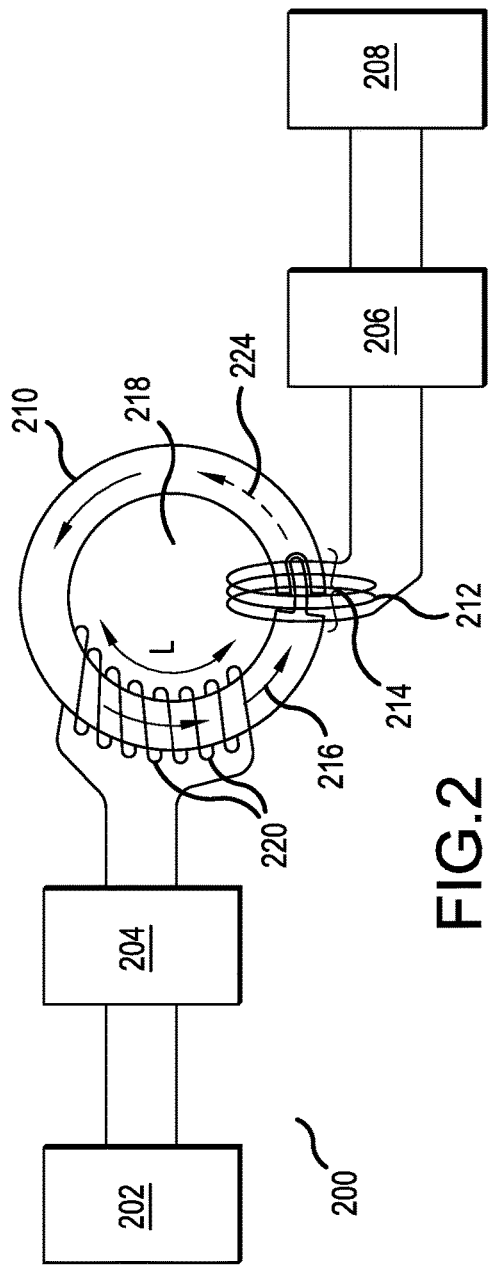

ically removed or specially designed in case of MRI (Magnetic Resonance Imaging). Moreover, since the attractive forces between the magnets are limited, the external unit may move from the desired position and even fall down as a result of fast movements of the head (for example, when the patient jumps).

IMPLANTABLE MEDICAL DEVICE COMPRISING A WIRELESS TRANSCUTANEOUS LINK

FIELD

The present disclosure relates to an implantable medical device comprising a transcutaneous link. In particular, the disclosure relates to an implantable medical device, such as a hearing aid, comprising a wireless transcutaneous link for transmitting power and/or data over the link comprising a coupling between a transmitter coil and an implantable receiver coil, wherein a coupling coefficient between the transmitter coil and the implantable receiver coil is substantially improved.

BACKGROUND

Any discussion of the prior art throughout the specification in no way be considered as an admission that such prior art is widely known or forms parts of common general knowledge in the field.

Medical devices having one or more implantable unit, generally referred to as implantable medical devices, have provided a wide range of benefits to patients over recent decades. In particular, devices such as implantable hearing aids, implantable pacemakers, defibrillators, eye implant, retina implant, heart pump, drug delivery systems, gastric implant, nerve stimulators, brain stimulators, functional electrical stimulation devices, such as cochlear prostheses, organ assist or replacement devices, and other partially or completely-implanted medical devices, have been successful in performing life-saving and/or lifestyle enhancement functions for a number of years.

As such, the type of implantable devices and the range of functions performed thereby have increased over the years. For example, many such implantable medical devices often include one or more instruments, apparatus, sensors, processors, controllers or other functional mechanical, electrical or electronic components that are permanently or temporarily implanted in a patient to perform diagnosis, prevention, monitoring, treatment or management of a disease or injury or symptom thereof, or to investigate, replace or modify of the anatomy or of a physiological process. Many of these implantable components receive power and/or data over a wireless transcutaneous link from external units that are part of, or operate in conjunction with, the implantable unit.

The wireless transcutaneous link is conventionally realized as an inductive link, with an external unit comprising a transmitter coil and an implantable unit comprising a receiver coil. Typically, the receiver coil is implanted, for example in an artificial cavity created in the mastoid region or below the skin, and the external unit includes a component having a disc-like shape that is attached to the patient's head in a detachable manner at a position opposite to the implanted receiver coil such that the two coils are in parallel planes on both sides (external and implantable positions) of the skin. The external unit typically includes at least one retention magnet that cooperates with an implanted retention magnet in order to keep the external unit at the correct position over the receiver coil such that the transmitter coil is axially aligned to the receiver coil, i.e. coil axis of the two coils are aligned to each other.

However, such fixation of the external unit via magnetic forces causes a relatively high weight of the external unit and also a relatively large size of the external unit. This is not only uncomfortable for the user but also aesthetically unattractive. In addition, the implanted magnet has to be surgically removed or specially designed in case of MRI (Magnetic Resonance Imaging). Moreover, since the attractive forces between the magnets are limited, the external unit may move from the desired position and even fall down as a result of fast movements of the head (for example, when the patient jumps).

For a conventional coil arrangement where the transmitter coil and the receiver coil are either sides of the skin and in parallel planes, the coupling coefficient is very low because most of the magnetic field lines that the transmitter coil generates is not picked up by the receiver coil, thus leading to poor energy transfer efficiency. In addition, as the two coils are located on either side of the skin, any change in coil separation, for example by way of increase in skin thickness, may result in rapid drop in the coupling coefficient between the two coils. In view of the efficiency problem, the external unit usually includes a relatively huge battery compartment or multiple batteries so that the implantable medical device is useable for a usage period that doesn't cause annoyance for the user, for example requiring the user to frequently change batteries or recharge the battery compartment. Besides making the external unit aesthetically less appealing, the additional weight of the battery compartment or multiple batteries also require a stronger retention magnet that may possibly lead to discomfort and in extreme cases irritation or infection of the skin that is under constant magnetic attraction force generated between the retention magnet and implantable magnet.

Accordingly, the present disclosure provides an alternative coil arrangement for a wireless transcutaneous link and discloses an implantable medical device that includes a wireless transcutaneous link where one or more of the above-mentioned shortcomings are addressed.

SUMMARY

According to an embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, and a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and when the loop structure is attached using the fixation unit, at least a substantial number of magnetic field lines generated in response to excitation of the transmitter coil passes through the implantable receiver coil.

The transmitter coil and the implantable coil individually comprises a number of turns. The number of turns in the transmitter coil and the receiver coil may be same or different.

In an embodiment, the loop structure is defined by a geometrical shape that includes a closed curve, defining a closed loop structure, wherein a point moving along the closed curve forms a path from a starting point to a final point that coincides with the starting point when the closed curve is in a closed mode. In one embodiment, the closed curve may include a single part loop structure comprising an openable section that includes a primary end and a secondary end. The openable section is attached to rest section of the loop structure at the primary end and is adapted to open the openable section at the secondary end (i.e. an open mode is defined when the openable section is open) to allow access to the hollow section and positioning of the part of the body part within the hollow section. The closed mode is defined when the openable section is engaged with rest of the section at the secondary end to form the closed curve. Alternatively, the closed curve may include multi-parts loop structure wherein the multi-parts includes a plurality of detachable parts, such as a first sub-part and a second sub-part, that are configured to attach with one another to form a closed loop structure. The closed mode is defined when the plurality of detachable parts is attached to one another. Accordingly, an open mode may be defined when the plurality of detachable parts is not attached to one another and in the open mode, the loop structure is adapted to allow positioning of the part of the body part within the hollow section of the loop structure. This may be achieved when the loop structure is in the open mode.

In another embodiment, the loop structure is defined by a geometrical shape that includes an open curve, defining an open loop structure, wherein a point moving along the open curve forms a path from a starting point to a final point that is proximal to but separated from the starting point by a distance. The distance is typically a function of a thickness of the body tissue and/or skin to which the loop structure is attached, i.e. the distance is configured such that the loop structure is attachable to the user's body. The distance is selected from a group consisting of a length that is smaller than the thickness of the body tissue, a length that is more than the thickness of the body tissue but is adapted to be reduced such that the changed length is smaller than the thickness of the body tissue, and a length that is less (may even be close to zero) than the thickness of the body tissue but is adapted to be increased such that the changed length is slightly smaller than the thickness of the body tissue. In these alternatives, it is apparent that the length smaller or slightly smaller than the thickness of the body tissue is adapted in a way such that a compressive retention force between a first end (i.e. first point of the geometrical shape) and a second end (i.e. second point of the geometrical shape) against the body tissue is applied. The skilled person would appreciate that the distance may be changed in order to achieve a balance between reliable retention and user comfort, especially for extended wearing of the medical device.

In different embodiments, the loop structure may include shape that is selected from a circular, elliptical, rectangular, square, polygonal shape, curved shape or a combination thereof.

The term "proximal" to the receiver coil indicates that the transmitter coil is positioned close to the implantable receiver coil such that an inductive coupling between the transmitter coil and the implantable receiver coil is achieved. This is achieved when the loop structure is attached to the body part using the fixation unit.

The term "around" a body part indicates that the fixation unit is configured to attach the loop structure such that the loop structure extends, with or without piercing the body tissue, between a posterior side and an anterior side of the body part and with the part of the body part being positioned in the hollow section of the loop structure. The anterior side may be understood as front side relative to the posterior side, which may be understood as back side. The term "around" a body part may also be defined by the fixation unit being configured to attach the loop structure such that the loop structure extends in a way that the first end and the second end of loop structure is adapted to sandwiched a body tissue with the part of the body part being positioned in the hollow section of the loop structure. The term "around" a body part may also be defined by the fixation unit being configured to attach the loop structure such that the loop structure extends in a way that the loop structure pierces through the body part with the part of the body part being positioned in the hollow section of the loop structure.

In one embodiment, the term "hollow section" is defined by an area that is enclosed by the closed curve when the closed curve is in the closed mode. In another embodiment, the hollow section is defined by an area that the open curve in combination with an imaginary line joining the distance separating the first point (first end of the loop structure) and second point (second end of the loop structure) encloses.

The term "positioned" within the hollow section is defined by the part of the body part being received within the area enclosed by the closed curve or within the area enclosed by the open curve in combination with the imaginary line.

The term "generated in response to excitation of the transmitter coil" refers to creation of alternating magnetic field on the transmitter coil when the transmitter coil is supplied with an electrical current. Thus, the term "excitation" comprises supplying the transmitter coil with an electrical current. According to the principle of magnetic induction, the alternating magnetic field lines is picked by the implantable receiver coil and converted into an electrical current in the implantable receiver coil. The generated electrical current depends on the coupling between the transmitter and implantable receiver coil, as expressed by the coupling coefficient. A higher coupling coefficient means a more efficient transfer link.

The term "a substantial number of magnetic field lines" passing through the implantable receiver coil refers to an electromagnetic coupling between the transmitter coil and the implantable efficiency such that a coupling coefficient between the external coil and the implantable receiver coil is at least 0.5, preferably 0.6, more preferably 0.7, even more preferably 0.8 and the most preferably 0.9. It is apparent that in embodiments utilizing closed loop structure, leakage of field lines/magnetic flux is minimized and a significantly higher coupling coefficient of at least 0.7, preferably 0.8 and even more preferably 0.9 is achieved. In embodiments utilizing the open loop structure, the sandwiched skin and body tissue may result in some magnetic flux/field lines leakage, thus leading to a reduction in coupling coefficient when compared to the closed loop structure. Nonetheless, even in such embodiments, a coupling coefficient of at least 0.5, preferably at least 0.6 and more preferably 0.7 is achieved. Despite the coupling coefficient in the open loop structure embodiments being a function of thickness of the skin and body tissue, the coupling coefficient is still higher than the conventional wireless transcutaneous link comprising parallel transmitter coil-receiver coil set up because the open loop structure is adapted to guide the magnetic field lines generated in response to excitation of the transmitter coil in a focused way towards the implantable receiver coil. The term may also refer to "a substantial number of magnetic field lines" the magnetic field lines generated in response to the excitation of the transmitter coil being primarily concentrated within the loop structure and also passing through the implantable receiver coil. The substantial number of magnetic field lines may also be understood as a substantial amount of magnetic flux, which is generated in response to excitation of the transmitter coil.

In different embodiments, the implantable processing unit is an implantable processor and/or an implantable stimulator that is configured to generate an output. The output is configured to generate perceivable stimulation for the user. For example, such perceivable stimulation includes perception of sound in case of implantable hearing aids. For the medical device comprising a hearing aid, the output may include a stimulation pulse (usually frequency specific) or signal for generating vibrational force (usually frequency specific). In an embodiment, the implantable processing unit comprises a power controller adapted to control utilization of power received at the implantable receiver coil.

The term "one of the components of the implantable unit" includes one or more of processing unit, rechargeable battery, vibrator, vibratory unit, electrode array, pump, sensor, drug capsule and any other implantable component of the medical device.

In different embodiments, the phrase "control functionalities of at least one of the components of the implantable unit" includes i) the processing unit generating, in accordance with the data signal, parameters (like stimulation pulse or signal for generating vibrational force) for producing perceivable stimulation like sound perception in cochlear implant or in bone conduction hearing aid, and/or ii) electrode array delivering electrical charges that is dependent upon the generated parameter (stimulation pulse), and/or iii) vibrator or vibratory unit generating vibrations that is dependent upon the generated parameter (signal for generating vibrational force), and/or iv) a sensor collecting in vivo biological data, and/or v) a pump, such as a continuous pump or an intermittent pump, pumping bodily fluid such as blood within the body or releasing a drug from an implantable capsule/container containing the drug, and/or vi) the rechargeable battery being adapted to be put in charging mode or operational mode. The charging mode is defined when the battery is being charged and operational mode is defined when the rechargeable battery is adapted to provide power to the implantable unit components like to the processing unit or electrode array or vibrator or vibratory unit or sensor or pump. The processing unit may also be configured to measure charge level of the rechargeable battery and trigger the charging mode when the measured charge level is below a minimum threshold level and/or trigger an operational mode when the measured charge level is above a predetermined level.

The phrase "utilize the received power" includes providing operational power to one or more of the processing unit, electrode array, vibrator, vibratory unit, pump, sensor and for recharging of the rechargeable battery.

In an embodiment, when the loop structure is attached using the fixation unit, at least a substantial number of magnetic field lines generated in response to excitation of the transmitter coil encircle the part of the body part received in the hollow section of the loop structure.

The loop structure is preferably a solid loop that is made up of a magnetic, like ferrite, material preferably having a high magnetic permeability. Such high magnetic permeability is at least 10, preferably at least 100, more preferably at least 1000. Such material may be selected from a group consisting of a ferrite materials, and soft iron. Other commercially available products under brand names VACOFLUX™, VACODUR™, VOCADUR S PLUS™, TRAFOPERM™, CRYOPERM™, PERMAX™, PERMENORM™ ULTRAPERM™, VACOPERM™, CHRONOPERM™, MEGAPERM™, MUMETALL™, RECOVAC™, and THERMOFLUX™, as produced by Vacuumschmelze GmbH & Co. KG or REMKO™ as produced by Uddeholm A/S may also be used. As the loop structure is made up of a magnetic material, most of the field lines are concentrated within the magnetic material and thus allow for a high coupling coefficient between the primary coil and the secondary coil. It would be apparent to the skilled person that a material of different magnetic permeability may also be used so long as the material has high enough magnetic permeability to guide the field lines generated in response to excitation of the transmitter coil in a focused way towards the implantable receiver coil in a way explained in this disclosure.

In several embodiments, the loop structure comprises the fixation unit. In other words, the fixation unit is part of the loop structure and may define a part of the loop axis.

In an embodiment, the fixation unit is adapted to attach the loop structure with respect to the implantable receiver coil in an arrangement such that one section of the implantable receiver coil is positioned within the hollow section of the loop structure whereas the other section of the implantable receiver coil is positioned outside the hollow section of the loop structure.

In an embodiment, the lengthwise distance between the transmitter coil and receiver coil is more than diameter of the receiver coil. Additionally, or alternatively, the lengthwise distance between the transmitter coil and receiver coil is more than diameter of the transmitter coil. In these embodiments, the lengthwise distance includes the shortest distance from at least one of the ends of the transmitter coil on the loop structure along length of the loop structure to planar surface of the implantable receiver coil.

In an embodiment, the medical device does not include an implantable retention magnet for attaching the external unit. Thus, the fixation unit is adapted to prevent utilizing an implantable retention magnet to attach the loop structure to the user's body. This is particularly useful for MRI as the need to remove an implantable magnet or specially design an implantable retention magnet is obviated.

In an embodiment, at least one turn of the transmitter coil is non-parallel to the implantable receiver coil. Additionally, or alternatively, at least one turn of the transmitter coil is non-coaxial with the receiver coil.

In an embodiment, the transmitter coil and the implantable receiver coil are adapted to be arranged relative to each other such that the coupling coefficient between the transmitter coil and the implantable receiver coil is independent of orientation of the transmitter coil with respect to the implantable receiver coil. The orientation refers to the co-axial and/or planar alignment of the transmitter coil with respect to the implantable receiver coil.

In an embodiment, the fixation unit is configured to attach the loop structure proximal to the implantable receiver coil such that a loop axis or an extrapolated loop axis of the loop structure passes through the implantable receiver coil. In one embodiment disclosing a loop structure defined by the closed curve geometrical shape, the loop axis is defined as an axis that runs along the entire length of the loop structure.

In another embodiment disclosing a loop structure defined by the open curve geometrical shape, the extrapolated loop axis is defined by an axis that runs along the entire length of the loop structure and an imaginary line joining the distance separating the first point (first end of the loop structure) and second point (second end of the loop structure).

The medical device according to any of the preceding claims, wherein the fixation unit is configured to attach the loop structure around the body part such that the loop structure and the implantable receiver coil are arranged in an interlocked hopf link configuration. As most (substantial number) of the field lines are concentrated within the loop structure, an interlocked hopf link configuration between the loop structure and the implantable receiver coil allows for obtaining a high coupling coefficient between the transmitter coil (wound around the loop structure) and the implantable receiver coil. In one embodiment disclosing a loop structure defined by the closed curve geometrical shape, the hopf link defines a loop structure that is mechanically locked together with the implantable receiver coil in a hopf configuration. In another embodiment disclosing a loop structure defined by the open curve geometrical shape, the hopf link defines a loop structure that is locked together with the implantable receiver coil by the imaginary line of the extrapolated loop axis. In these embodiments, i) one of the loop structure (closed loop structure) or imaginary line of the extrapolated loop axis (open loop structure) is adapted to pass through center of the implantable receiver coil, and/or ii) the implantable receiver coil is adapted to pass through center of the loop structure. Alternatively, i) one of the loop structure (closed loop structure) or imaginary line of the extrapolated loop axis (open loop structure) is adapted to prevent passing through center of the implantable receiver coil, and/or ii) the implantable receiver coil is adapted to prevent passing through center of the loop structure.

In an embodiment, the fixation unit is configured to attach the loop structure around the body part such that i) the loop structure and the implantable receiver coil are arranged in an interlocked first hopf link configuration, and ii) the loop structure and the transmitter coil are arranged in an interlocked second hopf link configuration. In this embodiment, the first hopf link configuration includes any or all the features disclosed for interlocked hopf link configuration from the preceding paragraph. Because of the first hopf link configuration and second hopf link configuration, a substantial number of magnetic field lines are concentrated within the loop structure and passes through the receiver coil, thereby substantially improving the coupling coefficient.

In an embodiment, the implantable receiver coil is in a first plane and the loop structure is along a second plane, the first plane and the second plane being at least substantially perpendicular to each other.

In an embodiment, the loop structure includes an openable closed loop structure comprising a section that is configured to penetrate through the body part at least at one point of the body part. As described earlier, the closed loop structure may be defined by the closed curve. In an embodiment, the openable closed loop structure includes a closed loop structure comprising an openable section that includes a primary end and a secondary end. The openable section is attached to rest section of the loop structure at the primary end and adapted to open the section at the secondary end (i.e. defining an open mode when the section is opened) to allow access to the hollow section and positioning of the part of the body part within the hollow section. The closed mode is defined when the openable section is engaged with rest of the section at the secondary end to form the closed curve. The openable section is adapted (typically through use of the fixation unit) to penetrate through the body part at least at one point of the body part. In particular, the secondary end of the openable section is adapted to penetrate through the body part at least at one point of the body part. Alternatively, the openable closed loop structure may include multi-parts loop structure wherein the multi-parts includes a plurality of detachable parts that are configured to attach with one another to form a closed loop structure. The closed mode is defined when the plurality of detachable parts is attached to one another. Accordingly, an open mode may be defined when the plurality of detachable parts is not attached to one another and in the open mode, the loop structure is adapted to allow positioning of a part of the body part within the hollow section of the loop structure. The plurality of detachable parts individually includes at least a first end and a second end. The first ends of the plurality of detachable parts and the second ends of the plurality of detachable parts are adapted to connected to each other respectively to form a closed loop structure. At least one of the first ends or the second ends of at least one of the plurality of detachable parts is adapted to penetrate through the body part at least at one point of the body part.

In any of the embodiments for the openable closed loop structure, the openable closed loop structure is adapted to penetrate through the body part at least at one point of the body part. Such at least one point includes at least one hole that is provided at the body part and the implantable coil is adapted to be implanted and arranged around one or more holes of the at least one hole. The term "around" refers to the implantable receiver coil being adapted to encircle the one or more holes of the at least one hole.

In another embodiment, the loop structure comprises an openable open loop structure comprising a slit having a first slit end configured to abut a first skin surface of the user and a second slit end, opposite to the first slit end, configured to abut a second skin surface of the user, the first skin surface and the second skin surface being separated by a body tissue. As described earlier, the open loop structure may be defined by the open curve. The first slit end and the second slit end are generally separated by a distance, which is typically a function of thickness of the body tissue to which the loop structure is attached.

The distance is selected from a group consisting of i) a length that is smaller than the thickness of the body tissue, ii) a length that is more than the thickness of the body tissue but is adapted to be reduced such that the changed length is smaller than the thickness of the body tissue, and iii) a length that is less (may even be close to zero) than the thickness of the body tissue but is adapted to be increased such that the changed length is slightly smaller than the thickness of the body tissue. The openable open loop structure includes means (typically part of the fixation unit) adapted to change the distance in order to allow positioning the part of the body part within the hollow section of the loop structure. For example, the means is adapted to increase the distance in the situations i) or iii) and to reduce the distance in situation ii).

In any of the embodiments for the openable open loop structure, the length smaller or slightly smaller than the thickness of the body tissue is adapted in a way such that a compressive retention force between a first slit end and second slit end against the body tissue is applied. The distance may be further adapted in order to achieve a balance between reliable retention and user comfort, especially for extended wearing of the medical device. In an embodiment, the first slit end and the second slit end are configured to abut the first skin surface at a first point and the second skin surface at a second point, opposite to the first point, and the implantable coil is adapted to be implanted and arranged around the first point and the second point. The term "around" refers to the implantable receiver coil being adapted to encircle the body tissue sandwiched between the first end (point) and the second end (point). The body tissue encircle by the receiver coil is typically includes the tissue part that is passed through by the imaginary line of the extrapolated loop axis.

The first slit end is adapted to face a first planar side of the implantable receiver coil; and a second slit end is adapted to face a second planar side, opposite to the first planar side, of the implantable receiver coil. Thus, the first slit end is adapted to abut the first skin surface at the first point and the second slit end is adapted to abut the second skin surface at the second point.

In an embodiment, diametric dimensions of the implantable receiver coil is at least same as width of the loop structure. The width refers to cross-sectional thickness of the loop structure. In another embodiment, planar area of the implantable receiver coil is at least same as the cross sectional area of the loop structure at an interface of the loop structure. The cross sectional area of the loop structure at the interface of the loop structure may include i) cross sectional area at the first end and or the second end of the loop structure, or ii) cross sectional area of the section of the loop structure that penetrates through the body part at least at one point of the body part.

In an embodiment, the implantable unit comprises an implantable magnetic core that is configured to be positioned within an area enclosed by a perimeter of the implantable receiver coil. The magnetic core allows for an increased number of magnetic field lines being picked up the receiver coil, thereby further increases the coupling coefficient between the transmitter coil and the implantable receiver coil.

In an embodiment, a substantial number of magnetic field lines generated in response to excitation of the transmitter coil are generated within the loop structure. As the loop structure is made of a magnetic material, the field lines are concentrated within and along the length of the loop structure. In the closed loop structure, such length would include the entire length of the loop structure. In the open loop structure, such length would include the entire length of the loop structure in combination with length of the imaginary line that connects two ends of the loop structure, the two ends being configured to be positioned on either side of the body part. It is understandable that the imaginary line in physical context would be contained by skin and body tissue that is sandwiched between the two ends. Although the sandwiched skin and body tissue may result in a reduction in coupling coefficient because of leakage when compared to using the closed loop structure. Nonetheless, the skilled person would appreciate that despite some leakage, a substantial amount of magnetic field lines generated in response to excitation of the transmitter coil would still follow the path of the imaginary line because of the short distance between first end and the second end of the loop structure, in particular, when the implantable magnetic core is configured to be positioned within the area enclosed by the perimeter of the implantable receiver coil.

In an embodiment, at least one turn of the transmitter coil is non-parallel to the implantable receiver coil. As the transmitter coil is wound around the loop structure, the alignment coaxial and/or parallel alignment of the transmitter coil with respect to the implantable receiver coil is not critical in order to achieve high coupling coefficient. Thus, the transmitter coil and the implantable receiver coil are arranged relative to each other such that the coupling coefficient between the transmitter coil and the implantable receiver coil is independent of orientation of the transmitter coil with respect to the implantable receiver coil. This is made possible because the coupling is dependent upon the positioning of the loop structure in relation to the implantable receiver coil. The "orientation" refers to the co-axial and/or planar alignment of the transmitter coil with respect to the implantable receiver coil.

In an embodiment, the loop structure comprises a first sub-structure and a second sub-structure, the first sub-structure and second sub-structure being configured to operationally connect with each other to form the openable closed loop structure or openable open loop structure. In an embodiment, the first sub-structure and the second sub-structure individually includes at least a first end and a second end. The first ends of the first sub-structure and the second sub-structure and the second ends of the first sub-structure and the second sub-structure are adapted to connect to each other respectively to form the openable closed loop structure. Alternatively, the one of the first ends of the first sub-structure and the second sub-structure or the second ends of the first sub-structure and the second sub-structure are adapted to connect to each other respectively to form the openable open loop structure with a distance between one of the first end-second end pair.

In an embodiment, the fixation unit is selected from a group consisting of a non-magnetic fixation unit and a fixation mechanism that is adapted to attach the loop structure to a user's body independent of any cooperation (interaction) with the implantable unit. Such cooperation overcomes the requirement of conventionally known systems where the implantable retention magnet cooperates with an external retention magnet for attaching the external unit to the user's body.

In an embodiment, the fixation unit is selected from a group consisting of a clamp mechanism, spring mechanism, piercing pin mechanism, snap-coupling mechanism between the first sub-structure and second sub-structure, a magnetic coupling mechanism between the first sub-structure and second sub-structure, and a combination thereof.

In an embodiment, the body part includes an earlobe such that the receiver coil is configured to be implanted within the earlobe of the user; and the fixation unit is configured to attach the loop structure around the earlobe such that the loop structure extends, with (such as in the closed loop structure) or without (such as in open loop structure) piercing through the earlobe, between a posterior side and an anterior side of the earlobe and with a part of the ear lobe being positioned in the hollow section of the loop structure. A section of the implantable coil is received in the hollow section of the loop structure whereas rest section of the implantable coil is outside the hollow section of the loop structure.

In an embodiment, the body part includes periumbilical region of the user such that the receiver coil is configured to be implanted within the periumbilical region preferably around an umbilicus of the user; and the fixation unit is configured to attach the loop structure around a skin in the periumbilical region such that the loop structure extends, with (such as in the closed loop structure) or without (such as in open loop structure) piercing through the skin, between a posterior side and an anterior side of the skin and with a part of the skin being positioned in the hollow section of the loop structure. A section of the implantable coil is received in the hollow section of the loop structure whereas rest section of the implantable coil is outside the hollow section of the loop structure.

In different embodiments, the body part may include other implantation sites on the user's body such as tragus, body tissue over mastoid region, superciliary arch, and any other suitable location.

In embodiments utilizing the closed loop structure, the fixation unit is adapted to penetrate through the body part at least at one point of the body part. The body part is selected such that the skin at the body part is adapted i) to allow penetration of the fixation unit through an opening/hole at the at least one point, and ii) to grow at periphery of the through opening/hole and sealing off the body tissue around the at least one point against ingress of material like dirt, sweat, etc. Such growth of skin at the periphery may occur over a period of healing time. The growth at the periphery and sealing of the body tissue may be comparable to healing of an earhole (puncture in the earlobe) after a successful cosmetic earlobe piercing.

In an embodiment, the processing unit is configured to process the received data signal and generate an output. The output is configured to generate perceivable stimulation for the user. For example, such perceivable stimulation includes perception of sound in case of implantable hearing aids. The medical device thus may be selected from a group consisting of one or more of i) an implantable hearing aid comprising a cochlear implant comprising an implantable electrode array configured to be positioned within a cochlea of the user, the electrode array being configured to deliver electrical charges in accordance with the output, ii) an implantable hearing aid comprising an auditory transmodiolar implant comprising an implantable electrode array configured to be positioned within a modiolus of the user, the electrode array being configured to deliver electrical charges in accordance with the output, iii) an implantable hearing aid comprising an auditory brainstem implant comprising an implantable electrode array (typically provided as a pad) configured to be implanted directly onto brainstem, the electrode array being configured to deliver the electrical charges in accordance with the output, iv) an implantable hearing aid comprising a bone conduction hearing aid comprising an implantable vibrator configured to be attached to skull of the user, the vibrator being configured to generate vibrations in accordance with the output, v) an implantable hearing aid comprising a middle ear implant comprising a vibratory unit configured to attach to one of the bones of the middle ear and/or to one of the windows of the cochlea, the vibratory unit being configured to generate vibrations in accordance with the output, vi) an artificial pacemaker comprising an electrode array configured to deliver electrical charges in accordance with the output.

vii) an implantable heart pump such as a ventricular assist device (VAD) comprising a pump configured to be attached to a user's heart, the pump being configured to provide blood flow within user's body, and vii) an implantable drug delivery system comprising an implantable capsule comprising a drug and a pump that is configured to attach to the implantable capsule and release, through a pumping action, a predefined amount of drug from the capsule to the user's body. In this embodiment, the drug delivery system may further include an implantable sensor that is configured to capture a biological data such as blood glucose level. The implantable processing unit is configured to receive the biological data and compare the received data with a stored normal range to determine a difference and accordingly, based on the difference, determine the amount of drug (predefined amount) to be released. The normal range, along with difference to amount of releasable drug may be stored as a look up table in a memory that the processing unit is configured to access. The processing unit is further configured, based on the determined predefined amount, to activate the pump (adapted to operationally connect to the capsule) for a duration that lets the predefined amount of the drug to be released from the capsule, viii) implantable deep brain stimulators or implantable nerve stimulators comprising an implantable electrode array configured to be implanted directly or indirectly onto the brain or nerve respectively, the electrode array being configured to deliver the electrical charges in accordance with the output comprising a stimulation pulse. The delivered electrical charges may be utilized to provide brain with information, viii) eye implants or retina implants comprising a camera for capturing images and an implantable electrode array configured to deliver electrical charges in accordance with the captured images, ix) an implantable cardioverter defibrillator comprising an electrode array (usually as electrical pads) configured to deliver electrical charges (for example by way of electrical shock) in accordance with a comparison of monitored rate and rhythm of the heart with a preset number. In this embodiment, the defibrillator may also include sensors in order to monitor the rate and rhythm of the heart, x) an implantable gastric stimulator configured to be implanted in an abdomen of the user and comprising an electrode array that is configured to deliver electrical charges (typically by way of mild electrical pulses) to nerves and smooth muscle of lower stomach of the user, and xi) an implantable brain computer interface system comprising an implantable sensor adapted to capture neural signals in response to brain activity. The system may further include an implantable transmitter coil adapted to transmit the neural signals as data packet over the wireless transcutaneous link to an external receiver coil. The implantable transmitter coil and external receiver coil is described later in embodiments relating to telemetry feedback data.

In the above paragraph, one or more of refers to use of a medical device or a combination thereof. For example, a cochlear implant may be used alone but may also be used in combination such as providing mechanical stimulation by way of bone conduction hearing aid at a first ear and an electrical stimulation by way of cochlear implant at a second ear of the user. In another example, the same user may be utilizing a cochlear implant as well as an implantable cardioverter defibrillator. Other such examples of combinations are within the scope of this disclosure. If the user is implanted with more than one medical device, a single transmitter coil-receiver coil pair may be used for providing data and/or power to the more than one implantable medical devices. In another embodiment, each of the implantable medical device may be provided with a dedicated transmitter coil-receiver coil pair. In either embodiment, the transmitter coil-receiver coil pair refers to the wireless transcutaneous link that is in accordance with this disclosure.

In embodiments where the medical device includes the implantable hearing aid, the external unit typically includes a microphone array adapted to capture sound from user's environment. The microphone array is configured to generate an electrical signal. The microphone array may be configured to provide direction-dependent signal processing in different beamforming modes. Beamforming involves processing sound received at the microphones of the array in such a way as to make the array act as a highly directional microphone. Additionally, the external unit may further include a filter bank, configured to receive the electrical signal, includes an array of frequency specific signal filters that separates the incoming electrical signal, such as speech or music, into the plurality of band pass limited electrical signals. Typically, the filter bank has a number of narrow frequency band filters with each filter associated with a specific band of audio frequencies. The incoming audio signal is thus filtered into the plurality of band pass limited electrical signals where each signal corresponds to the band of frequencies for one of the band pass filters.

The external unit includes the electronic unit comprising a processor configured to process the electrical signal or band pass limited electrical signals to compensate for hearing loss of the user, thus generating a processed electrical signal. The processor is further adapted to encode the processed electrical signal and transmit the processed electrical signal in form of the data signal over the wireless transcutaneous link from the transmitter coil to the implantable receiver coil. To achieve this, the external unit comprises a power source and the processor is configured to draw required current form the power source to excite (supply electrical current) the transmitter coil for generating magnetic lines required for transmission of the data signal. The implanted receiver coil is adapted to receive the data signal. The implantable processing unit is configured to decode the data signal and accordingly generate the output such as a stimulation pulse (usually frequency specific) or a signal for generating vibrational force (usually frequency specific). Depending upon the hearing aid type, the output is delivered to an implantable electrode or implantable vibrator or implantable vibratory unit in order to produce an electrical stimulation by way of delivery of electrical charges or generating vibrations. Additionally, the external processor may be configured to draw sufficient current from the power source for exciting the transmitter coil such that both data signal and power may be transmitted over the wireless transcutaneous link from the transmitter coil to the receiver coil. The processing unit is configured to utilize the power received at the implantable receiver coil for operation of at least one of the components of the implantable unit. The implantable unit may include an energy storage unit such as capacitors or rechargeable battery that is adapted to store the received power. The stored received power is utilized for the operation of one at least one of the components of the implantable unit.

In embodiments where the medical device includes the implantable hearing aid, the implantable unit may include a rechargeable battery. The external unit includes a power source that is adapted to excite the transmitter coil and transfer only power over the wireless transcutaneous link from the transmitter coil to the implantable receiver coil. The receiver coil is adapted to receive the power and the received power is used to charge the rechargeable battery, which is adapted to provide operational power at least one of the components of implantable unit including the processing unit. The implantable unit may further include, as disclosed earlier, a microphone array that is adapted to generate the electrical signal may apply beamforming techniques with our without filtering using the filterbank. The implantable processing unit is adapted to utilize the power received from the rechargeable battery and process the electrical signal to compensate for hearing loss of the user, thus generating a processed electrical signal (output). Depending upon the hearing aid type, the output is delivered to an implantable electrode or implantable vibrator or implantable vibratory unit in order to produce an electrical stimulation by way of delivery of electrical charges or generate vibrations.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and the fixation unit is adapted to attach the loop structure with respect to the implantable receiver coil in an arrangement such that one section of the implantable receiver coil is positioned within the hollow section of the loop structure whereas the other section of the implantable receiver coil is positioned outside the hollow section of the loop structure.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and the fixation unit is configured to attach the loop structure proximal to the implantable receiver coil such that a loop axis or an extrapolated loop axis of the loop structure passes through the implantable receiver coil.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and the fixation unit is configured to attach the loop structure around the body part such that the loop structure and the implantable receiver coil are arranged in an interlocked hopf link configuration.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil. The fixation unit is configured to attach the loop structure around the body part such that i) the loop structure and the implantable receiver coil are arranged in an interlocked first hopf link configuration, and ii) the loop structure and the transmitter coil are arranged in an interlocked second hopf link configuration.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part in a first plane, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil. When the loop structure is attached using the fixation unit, the loop structure is arranged in a second plane such that the first plane and the second plane are at least substantially perpendicular to each other.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and the loop structure comprises an openable closed loop structure comprising a section that is configured to penetrate through the body part at least at one point of the body part.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil. The loop structure comprises an openable open loop structure comprising a slit having a first end configured to abut a first skin surface of the user and a second end, opposite to the first end, configured to abut a second skin surface of the user, the first skin surface and the second skin surface being separated by a body tissue.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and diametric dimensions of the implantable receiver coil are at least same as width of the loop structure.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around the body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and at least one turn of the transmitter coil is non-parallel to the implantable receiver coil.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around a body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil. The loop structure comprises a first sub-structure and a second sub-structure, the first sub-structure and a second sub-structure being configured to operationally connect with each other to form the openable closed loop structure or openable open loop structure.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around a body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and a lengthwise distance between the transmitter coil and implantable receiver coil is more than at least one of diameter of the transmitter coil or diameter of the implantable receiver coil.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around a body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and the transmitter coil and the implantable receiver coil are arranged relative to each other such that the coupling coefficient between the transmitter coil and the implantable receiver coil is independent of orientation of the transmitter coil with respect to the implantable receiver coil.

According to another embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, a fixation unit configured to attach the loop structure to a user's body i) proximal to an implantable receiver coil that is configured to be implanted within a body part, and ii) around a body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and the fixation unit is adapted to prevent utilizing an implantable retention magnet to attach the loop structure to the user's body.

According to an embodiment, a medical device is disclosed. The medical device includes an external unit and an implantable unit. The external unit includes an electronic unit operationally coupled to a transmitter coil that is configured transmit power and/or data signal over a wireless transcutaneous link, a coil unit comprising a loop structure with the transmitter coil being wound around and along at least a part of length of the loop structure, and a fixation unit configured to attach the loop structure to a user's body i) proximal to an implantable receiver coil that is configured to be implanted within a body part, and ii) around a body part of a user such that a part of the body part is positioned in a hollow section of the loop structure. The implantable unit includes the implantable receiver coil configured to receive the power and/or data signal over the wireless transcutaneous link, a processing unit configured to i) process the received data signal to control functionalities of at least one of the components of the implantable unit, and/or ii) utilize the received power for operation of at least one of the components of the implantable unit. The wireless transcutaneous link includes a coupling between the transmitter coil and the receiver coil, and when the loop structure is attached using the fixation unit, at least a substantial number of magnetic field lines generated in response to excitation of the transmitter coil encircle the part of the body part received in the hollow section of the loop structure.

In one embodiment, the above disclosed embodiments are also applicable for telemetry whereby feedback is provided from an implantable unit to an external unit such as in a cochlear implant system. In this set up, the above disclosed embodiments may be modified such that the implantable receiver coil acts as an implantable transmitter coil and the transmitter coil of the external unit acts as an external receiver coil. These modifications are within the scope of this disclosure. Such set up would provide the same advantage in terms of coupling coefficient as embodiments disclosed earlier in this section.

Thus, in this embodiment, a medical device is disclosed. The medical device includes an implantable unit and external unit. The implantable transmitter coil is configured to transmit feedback telemetry data over a wireless transcutaneous link, and a processing unit configured to instruct the implantable transmitter coil to transmit the feedback telemetry data. The external unit includes a coil unit comprising a loop structure with an external receiver coil being wound around and along at least a part of length of the loop structure, the external receiver coil being adapted to receive the feedback telemetry data, a fixation unit configured to attach the loop structure to a user's body i) proximal to an implantable transmitter coil that is configured to be implanted within a body part, and ii) around a body part of a user such that a part of the body part is positioned in a hollow section of the loop structure. The wireless transcutaneous link comprises a coupling between the implantable transmitter coil and the external receiver coil, and when the loop structure is attached using the fixation unit, at least a substantial number of magnetic field lines generated in response to excitation of the implantable transmitter coil passes through the external receiver coil.

The feedback telemetry data may include measurements and other data regarding the operation and status of the implantable unit. The feedback telemetry data may also include in vivo biological data that includes, but not limited to, biological species and/or metabolites, glucose level, blood pressure, blood gas measurements, neural activity including signals directly from brain such as in a brain-computer interface, body temperature, and bodily part electrical activity. The in vivo biological data may be obtained using an implantable sensor that is configured to collect the in vivo biological data and transmit the collected biological data to the implantable processing unit, which is configured to encode the biological data and transmit the encoded data as a feedback telemetry data using the wireless transcutaneous link comprising the implantable transmitter coil and the external receiver coil, as disclosed in the preceding paragraph. The implantable sensor may include, but not limited to, biochemical sensors, mechanical sensors, electrical sensors, and neural prosthetic sensors.

Throughout the specification, unless stated explicitly otherwise, different disclosed embodiments should be considered combinable.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 1 illustrates a medical device comprising a conventional wireless transcutaneous link;

FIG. 2 illustrates an implantable medical device comprising a wireless transcutaneous link according to an embodiment of the disclosure;

DETAILED DESCRIPTION

Figure 3:
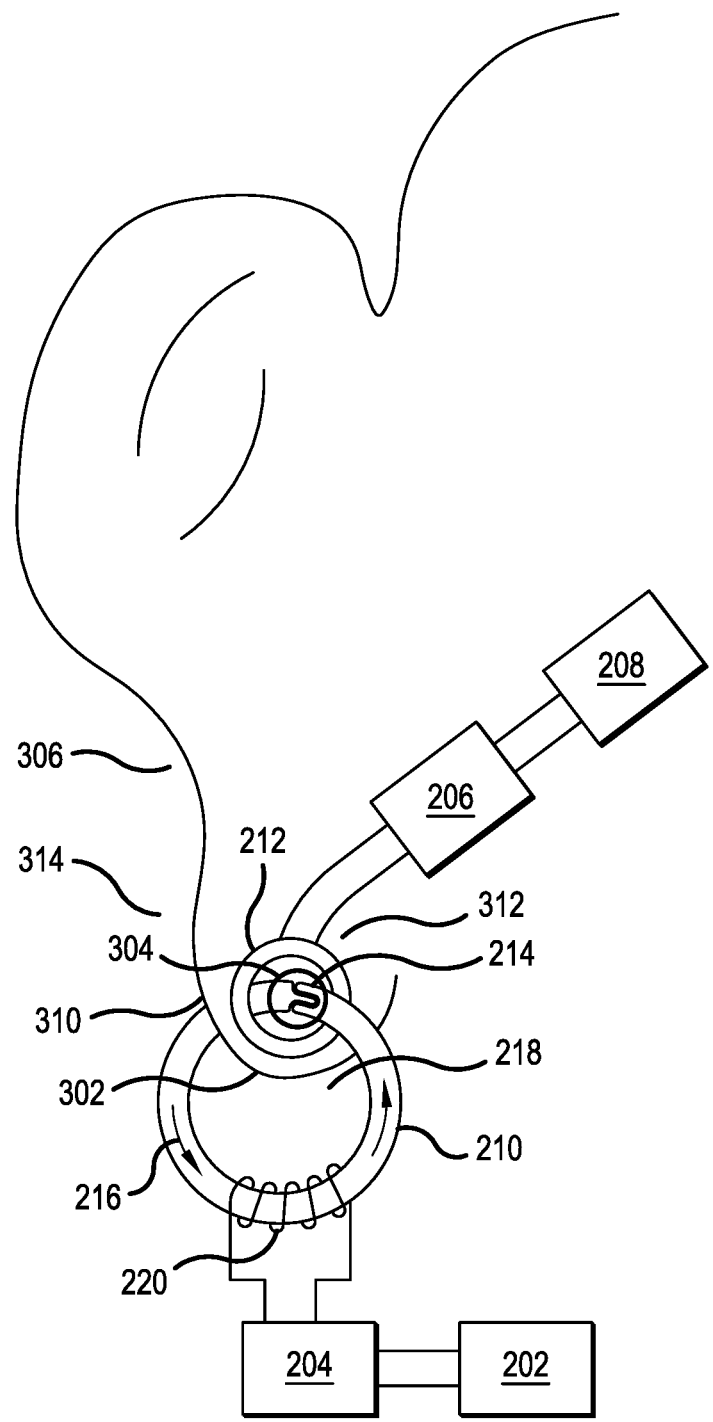
FIG. 3 illustrates an implantable medical device comprising a wireless transcutaneous link according to an embodiment of the disclosure.

The detailed description set forth below in connection with the appended drawings is intended as a description of non-limiting example embodiments of the method and system according to the present disclosure. Throughout the drawings, same or at least functionally comparable components are represented by same numerals. Throughout the text, different features are illustrated using the same figure. Although such separate features are combinable, such illustration of different features in same figure should not be construed in a way that these features are disclosed only in combination. By way of example, FIG. 8 discloses i) a magnetic core and ii) transmitter coil that is non-planar and non-coaxial with the receiver coil; these two features can be implemented separately and also in combination.

FIG. 1 illustrates a medical device 100 comprising a conventional wireless transcutaneous link. The device includes a primary (external) unit, external to the body, comprising a power source 102, an electronic unit 104 such as a power controller, and primary coil 108 through which an alternating current is passed, creating a time-varying magnetic field lines 114, 116. A secondary (implantable) unit, implantable under the skin and separable from the primary unit by thickness of the skin 112, contains a secondary coil 110. When the secondary coil 110 is placed in proximity to the time-varying magnetic field lines created by the primary coil, the varying flux induces an alternating current in the secondary coil, and thus power may be transferred inductively from the primary unit to the secondary unit. The transferred power may be utilized by an implantable processing unit 106 and load 108. In this set up, the coupling coefficient is very low because most of the magnetic field lines 116 that the transmitter coil generates is not picked up by the receiver coil and only a fraction of the magnetic field lines 114 pass through the secondary coil 110, thus leading to poor energy transfer efficiency. Also, the primary coil 108 is arranged in a detachable manner at a position opposite to the implanted receiver coil such using retention magnets. The external unit typically includes at least one retention magnet that cooperates with an implanted retention magnet in order to keep the external unit at the correct position over the receiver coil such that the transmitter coil is axially aligned to the receiver coil, i.e. coil axis of the two coils are aligned to each other. However, in view of poor coupling coefficient, the primary unit usually includes a relatively huge battery compartment or multiple batteries so that the implantable medical device is useable for a usage period that doesn't cause annoyance for the user. This results in increase in size of the primary unit and even stronger retention magnets and a heavier primary unit. This problem is further amplified because the two coils are located on either side of the skin, any change in coil separation, for example by way of increase in thickness of skin tissue 112, may result in rapid drop in the coupling coefficient between the two coils.

FIG. 2 illustrates an implantable medical device 200 comprising a wireless transcutaneous link according to an embodiment of the disclosure. The medical device 200 includes an external unit and an implantable unit. The external unit includes an electronic unit 204 operationally coupled to a transmitter coil 220 that is configured transmit power and/or data signal over a wireless transcutaneous link, a coil unit comprising a loop structure 210 with the transmitter coil 220 being wound around and along at least a part of length L of the loop structure 210, and a fixation unit 214 configured to attach the loop structure to a user's body (FIG. 3, 306) i) proximal to an implantable receiver coil 212 that is configured to be implanted within a body part (FIG. 3, 310), and ii) around the body part (FIG. 3, 310) of a user such that a part (FIG. 3, 302) of the body part is positioned in a hollow section 218 of the loop structure.

The implantable unit includes the implantable receiver coil 212 configured to receive the power and/or data signal over the wireless transcutaneous link, a processing unit 206 configured to i) process the received data signal to control functionalities of at least one of the components of the implantable unit, and/or ii) utilize the received power for operation of at least one of the components of the implantable unit. The wireless transcutaneous link includes a coupling between the transmitter coil 220 and the receiver coil 212, and when the loop structure 210 is attached using the fixation unit 214, at least a substantial number of magnetic field lines 216 generated in response to excitation of the transmitter coil 220 passes through the implantable receiver coil 212.

The medical device may further include a power source 202 that provides power to the electronic unit 204, which among other functionalities also provide power controlling functionality. The electronic unit 204 is configured to provide the transmitter coil with an alternating current, using the power source 202. The alternating current through the transmitter coil 220 produces a time-varying magnetic field lines 216, a substantial number of which are adapted to pass through the implantable receiver coil 212 when the loop structure 210 is attached to the body using the fixation unit 214. The time-varying magnetic field lines passing through the receiver coil 212 induces an alternating current in the receiver coil 212, and thus data and/or power may be transferred inductively from the external unit to the implantable unit. Because a substantial number of field lines are adapted to pass through the implantable receiver coil, the coupling coefficient is very high and independent of the separation between the transmitter coil and receiver coil and/or thickness of the body tissue. 208 represents a load such as an implantable electrode array or an implantable vibrator or an implantable vibratory unit.

In an embodiment, the above disclosed embodiment and following embodiment are also applicable for telemetry whereby feedback is provided from the implantable unit to the external unit such as in a cochlear implant system. In this set up, the above disclosed embodiment (and following embodiments) may be modified such that the implantable receiver coil 212 acts as an implantable transmitter coil and the transmitter coil 220 of the external unit acts as an external receiver coil. In such telemetry embodiments, the implantable processing unit 206 is configured to provide the implantable receiver coil 212 (acting as a transmitter coil) with an alternating current and a time varying magnetic flux 224 is created. When the loop structure 210 comprising wound transmitter coil (acting as an external receiver coil) is positioned on the body using the fixation unit 214, a substantial amount of the time varying magnetic flux 224 passes through the transmitter coil (acting as an external receiver coil) thus inducing alternating current in the transmitter coil (acting as an external receiver coil). Because a substantial amount of magnetic flux is adapted to pass through the transmitter coil (acting as an external receiver coil), the coupling coefficient is very high and independent of the separation between the transmitter coil and receiver coil and/or thickness of the body tissue and/or skin.

FIG. 3 illustrates an implantable medical device comprising a wireless transcutaneous link according to an embodiment of the disclosure. The fixation unit 214 is configured to attach the loop structure 210 to a user's body (ear) 306. The loop structure 210 is positioned proximal to an implantable receiver coil 212 that is configured to be implanted within a body part (ear lobe) 310, and ii) around the body part 310 of a user such that a part 302 of the body part is positioned in a hollow section 218 of the loop structure 210. Although it is not necessary for example in an open loop structure, but this embodiment illustrates that the fixation unit 214 is configured penetrate through the body part 310 at least at one point 304 of the body part. In this embodiment, the anterior side is the front side 312 and the posterior side is the back side 314.

Figure 9:
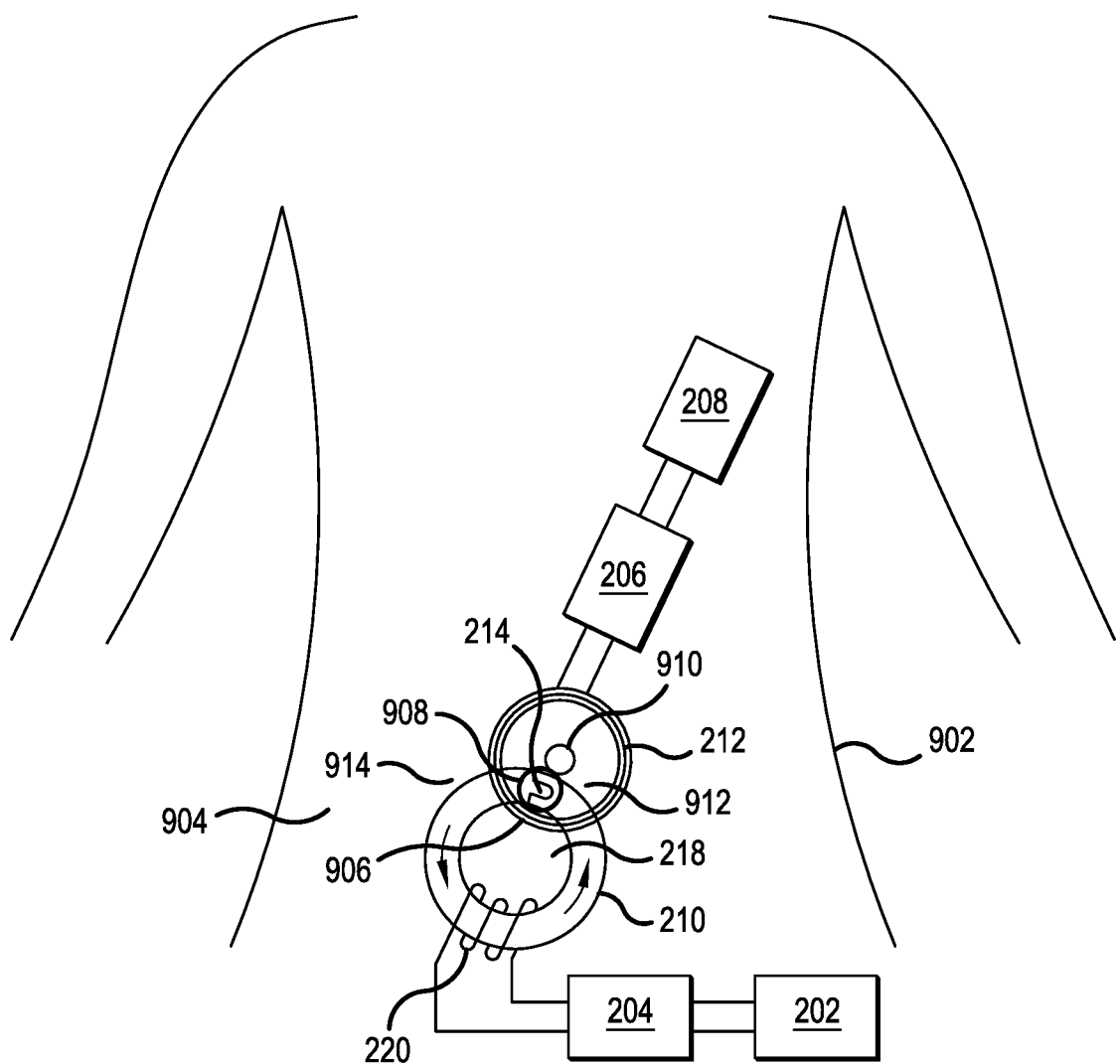
FIG. 9 illustrates an implantable medical device comprising a wireless transcutaneous link according to an embodiment of the disclosure.

FIG. 9 illustrates an implantable medical device comprising a wireless transcutaneous link according to an embodiment of the disclosure. The loop structure 210 is positioned proximal to an implantable receiver coil 212 that is configured to be implanted within a body part (periumbilical region) 904. The fixation unit 214 is configured to attach the loop structure 210 to a user's body (abdomen) 902 such that the loop structure 210 is positioned around a the body part (i.e. skin in the periumbilical region 904) and the loop structure extends, with (such as in the closed loop structure) or without (such as in open loop structure) piercing through the skin, between a posterior side 914 and an anterior side 912 of the skin and with a part of the skin 906 being positioned in the hollow section 218 of the loop structure 210. Although it is not necessary for example in an open loop structure, but this embodiment illustrates that the fixation unit 214 is configured penetrate through the body part at least at one point 908 of the body part. The implantable receiver coil is preferably configured to be implanted around the umbilicus 910 of the user.

In different embodiments, the body part may include other implantation sites on the user's body such as tragus, body tissue over mastoid region, superciliary arch, and any other suitable location.

Figure 4A:
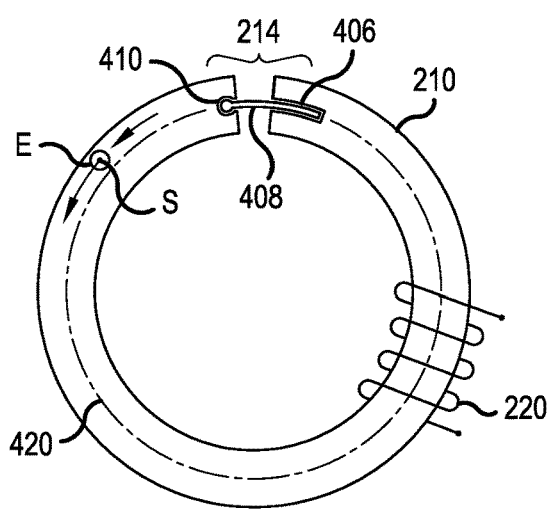
FIG. 4A illustrates a closed loop structure in a closed mode according to an embodiment of the disclosure.
Figure 4B:
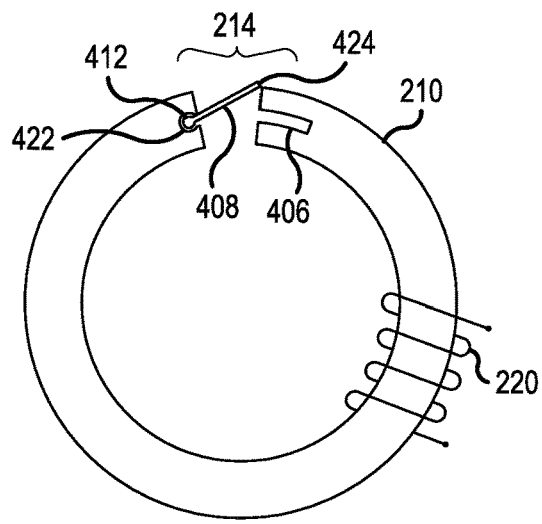
FIG. 4B, illustrates a closed loop structure in an open mode according to an embodiment of the disclosure.
Figure 4C:
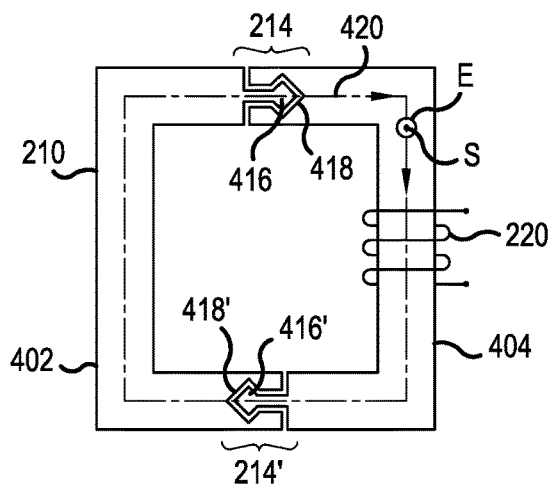
FIG. 4C illustrates a closed loop structure comprising a plurality of parts (in a closed mode) according to an embodiment of the disclosure.
Figure 4D:
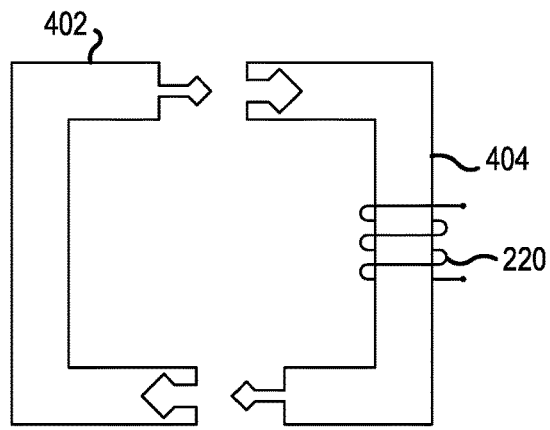
FIG. 4D illustrates a closed loop structure comprising a plurality of parts (in an open mode) according to an embodiment of the disclosure.

FIG. 4 illustrates a loop structure 210 that is defined by a geometrical shape that includes a closed curve, defining a closed loop structure (FIG. 4A, FIG. 4C, FIG. 4E), wherein a point S moving along the closed curve forms a path (counter clockwise direction starting from S) from a starting point S to a final point E that coincides with the starting point when the closed curve is in a closed mode (FIG. 4A, FIG. 4C). In one embodiment, the closed curve may include a single part loop structure (FIG. 4A, FIG. 4B, FIG. 4E) comprising an openable section (214, FIG. 4A through 4E) that includes a primary end (422, FIG. 4B) and a secondary end (424, FIG. 4B). The openable section is attached to rest section of the loop structure at the primary end and adapted to open the section at the secondary end. The open mode is defined when the openable section is open (FIG. 4B) to allow access to the hollow section and positioning of the part (302, FIG. 3) of the body part (310, FIG. 3) within the hollow section (FIG. 3, 218). The closed mode is defined when the openable section (214, FIG. 4B) is engaged with rest of the section at the secondary end (424. FIG. 4B) to form the closed curve. In one embodiment FIG. 4A and FIG. 4B, the fixation unit 214 comprises a pin 408, one end 412 of the pin is attached in swivel arrangement with the loop structure at a point 410 and another end of the pin 424 is adapted to be received in a hole 406 of the loop structure. The swivel action of the pin changes the mode of the loop structure from the closed mode (FIG. 4A) to the open mode (FIG. 4B) and vice versa. The pin 408 is adapted to penetrate through a body part at least at one point. In another embodiment of FIG. 4E, the fixation unit includes an openable section (clamp, 214) that includes a primary end 422 and a secondary end 424. The clamp 214 includes a threaded shaft 408 that is adapted to be interact with the thread 426 provided at the loop structure in order to screw the clamp in and out of the hole 406 using the handle 414 of the clamp. The shaft is adapted to penetrate through the body part at least at one point. FIG. 4E illustrates a closed mode but it is understandable that the clamp is adapted to be unscrewed and opened such that the loop structure is brought into an open mode to allow positioning of the part (FIG. 3, 302) of the body part (FIG. 3, 310) within the hollow section (FIG. 3, 218) of the loop structure 210.

Alternatively, the closed curve may include multi-parts loop structure (FIG. 4C and FIG. 4D) wherein the multi-parts includes a plurality of detachable parts, such as a first sub-part 402 and a second sub-part 404, that are configured to attach with one another to form a closed loop structure (FIG. 4C). In this embodiment, a snap-lock mechanism is disclosed in in order to attach the first sub part 402 with the second sub part 404. The snap lock mechanism includes one or more protrusion-hole pair that are adapted to detachably connect to each other. For example, the snap lock mechanism includes a protrusion (416, 416') at one of the sub-part (402, 404) that is adapted to be received in a hole (418, 418') in another of the sub part (404, 402). Although the illustration shows that each sub part includes a protrusion and a hole but it is equally possible that both the protrusions are provided at the same sub part and corresponding interacting holes provided at another sub part. In one embodiment, each protrusion is adapted to penetrate through the body at distinct point. For example, if one of the sub parts include both protrusions, then each protrusion is adapted to penetrate through the body at distinct spatially separated points. In another embodiment, only one protrusion is penetrate through the body at least at one point. The closed mode is defined when the plurality of detachable parts is attached to one another (FIG. 4C). Accordingly, in FIG. 4D, an open mode is defined when the plurality of detachable parts is not attached to one another and in the open mode, the loop structure is adapted to allow positioning of the part (FIG. 3, 302) of the body part (FIG. 3, 310) within the hollow section (FIG. 3, 218) of the loop structure 210. The skilled person would appreciate that other mechanisms other than snap mechanism for the fixation unit may also be employed.

The reference numeral 420 represents a loop axis that runs along length of the closed loop structure.

FIG. 5 discloses a loop structure 210 is defined by a geometrical shape that includes an open curve, defining an open loop structure, wherein a point S moving along the open curve forms a path (anti-clockwise direction starting from point S) from a starting point S to a final point E that is proximal to but separated from the starting point by a distance D.

The distance is typically a function of a thickness of the body tissue and/or skin to which the loop structure is attached, i.e. the distance is configured such that the loop structure is attachable to the user's body. In one embodiment (FIG. 5A), the fixation unit includes at least one spring 502 arranged between the inner surface of opposite arms of the loop structure such that the at least one spring is adapted to provide a pulling force between the two arms. The distance D is smaller than the thickness of the body tissue and the spring provides sufficient pulling force for providing a compressive retention force (FIG. 6B) between the first end (FIG. 6B, 602) and second end (FIG. 6B, 604) of the loop structure in order to attach the loop structure to the body. The user may apply a force countering and in excess of the pulling force in order to detach the loop structure from the body or to allow positioning of the part (FIG. 6, 302) of the body part (FIG. 6, 310) within the hollow section (FIG. 6, 218) of the loop structure 210. A balance between comfort and the retention force may be achieved based on choice of a spring with an appropriate spring constant. In another embodiment (FIG. 5B), the fixation unit includes a clamp 508 comprising a threaded shaft. The threaded shaft—loop structure thread pair 512 are adapted to cooperate with each other such that the distance D between the one end (FIG. 6B, 602 or 604) of the loop structure and an end face 510, opposite to the one end of the loop structure, is reduced by screwing the clamp towards the one end of the loop structure. Such reduction in the distance D allows for providing a compressive retention force between the one end of the loop structure and the end face 510 in order to attach the loop structure to the body. In this embodiment, the distance D is more than the thickness of the body tissue. A sufficient screwing of the clamp away from the one end of the loop structure may be used to detach the loop structure from the body part or to allow positioning of the part (FIG. 6, 302) of the body part (FIG. 6, 310) within the hollow section (FIG. 6, 218) of the loop structure 210. The advantage of the fixation unit comprising clamp is that the user may find a balance between comfort and compressive retention force. In yet another embodiment (FIG. 5C), the fixation unit relies on the bendability of the loop structure 210. The distance D is smaller than the thickness of the body tissue and the arms (526, 528) of the loop structure are adapted to be pulled apart in order to receive the part of the body part in the hollow section. The bendability of the loop structure at points 530 and 532 pulls the arms 526 and 528 towards each other such that a compressive retention force (FIG. 6B) between the first end (FIG. 6B, 602) and second end (FIG. 6B, 604) of the loop structure is applied in order to attach the loop structure to the body. The user may apply a force countering and in excess of the bendability based pulling force in order to detach the loop structure from the body to allow positioning of the part (FIG. 6, 302) of the body part (FIG. 6, 310) within the hollow section (FIG. 6, 218) of the loop structure 210. A balance between comfort and the retention force may be achieved based on choice of a bending properties of the loop structure. This embodiment is particularly simple to manufacture.

Figure 5A:
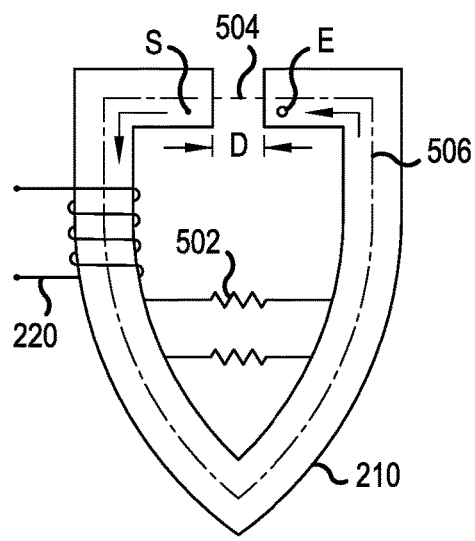
FIG. 5A illustrates an open loop structure according to an embodiment of the disclosure.
Figure 5B:
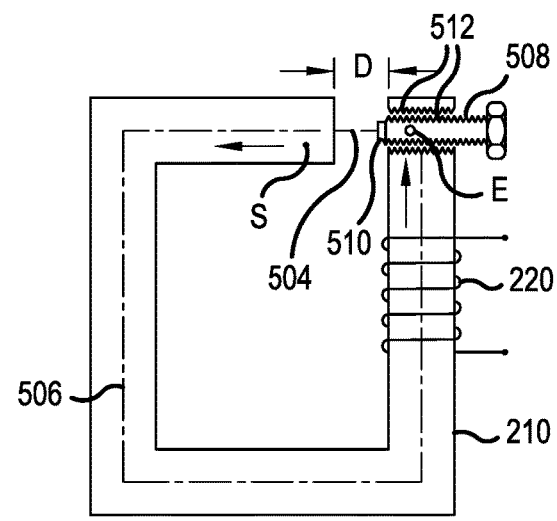
FIG. 5B illustrates an open loop structure according to an embodiment of the disclosure.
Figure 5C:
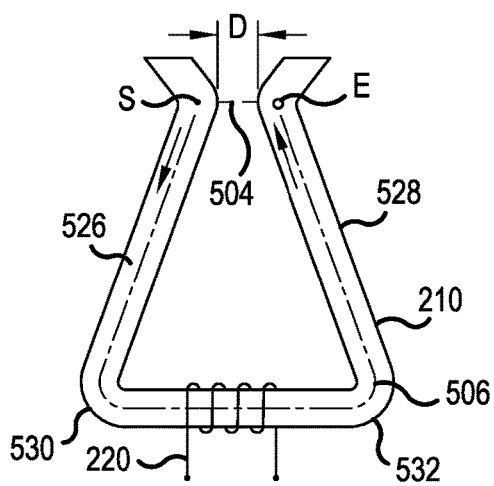
FIG. 5C illustrates an open loop structure according to an embodiment of the disclosure.
Figure 5D:
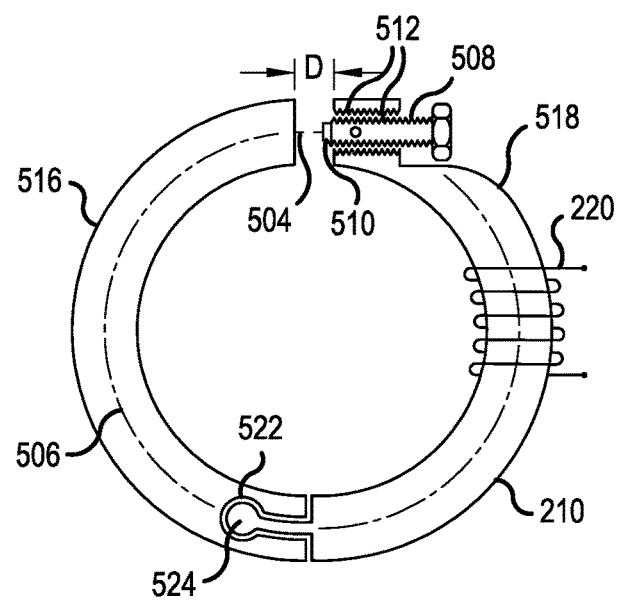
FIG. 5D illustrates an open loop structure comprising a plurality of parts according to an embodiment of the disclosure.

Alternatively, the open curve may include multi-parts loop structure (FIG. 5D) wherein the multi-parts includes a plurality of detachable parts, such as a first sub-part 516 and a second sub-part 518, that are configured to attach with one another to form the open loop structure (FIG. 5D). In one embodiment (FIG. 5D), a snap-lock mechanism is disclosed in order to attach the first sub part 516 with the second sub part 518, where one part 516 includes a hole 522 that is adapted to receive a protrusion 524 provided at the second part 518. The fixation unit includes a clamp mechanism that is similar in operation as the clamp disclosed in FIG. 5B. In another embodiment (not shown), a magnetic locking mechanism (instead of snap-lock mechanism 522-524 in FIG. 5D) is disclosed in order to attach the first sub part (516, FIG. 5D) with the second sub part (518, FIG. 5D). The Fixation unit includes a pair of magnets (instead of clamp mechanism of FIG. 5D) that provide a pulling force to reduce the distance (D, FIG. 5D), which is greater than thickness of the body tissue. The pulling force provides a compressive retention force in order to attach the loop structure to the body part. The loop can be detached simply by pulling and applying sufficient force overcoming the pulling magnetic force provided by the magnet pair. The choice of magnets in the magnet pair may provide a balance between reliability in retention and comfort level.

The numeral 506 illustrates an extrapolated loop axis by an axis that runs along the entire length of the loop structure 210 and an imaginary line 504 joining the distance D separating the first end (FIG. 6B, 602) of the loop structure 210 and second end (FIG. 6B, 604) of the loop structure 210.

Figure 4E:
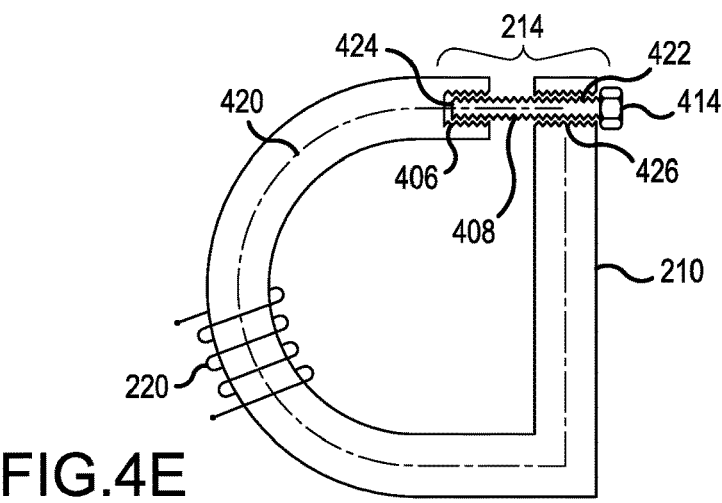
FIG. 4E illustrates a closed loop structure in a closed mode according to an embodiment of the disclosure.

In different embodiments, the loop structure 210 may include shape that is selected from a circular (FIGS. 4A, 4B, 5D), elliptical (FIG. 5A), rectangular (FIGS. 4C, 5B), square (FIGS. 4C, 5B), polygonal shape (FIG. 4C, 5B), curved shape (FIG. 4A, 4B, 5C) or a combination thereof (FIG. 4E).

In view of any of the FIGS. 3 through 6, it is evident that the fixation unit 214 is configured to attach the loop structure 210 proximal to the implantable receiver coil 212 (FIGS. 3, 6) such that a loop axis (FIG. 4, 420) or an extrapolated loop axis (FIG. 5, 506) of the loop structure passes through the implantable receiver coil (FIG. 3, FIG. 6, 212).

Figure 6A:
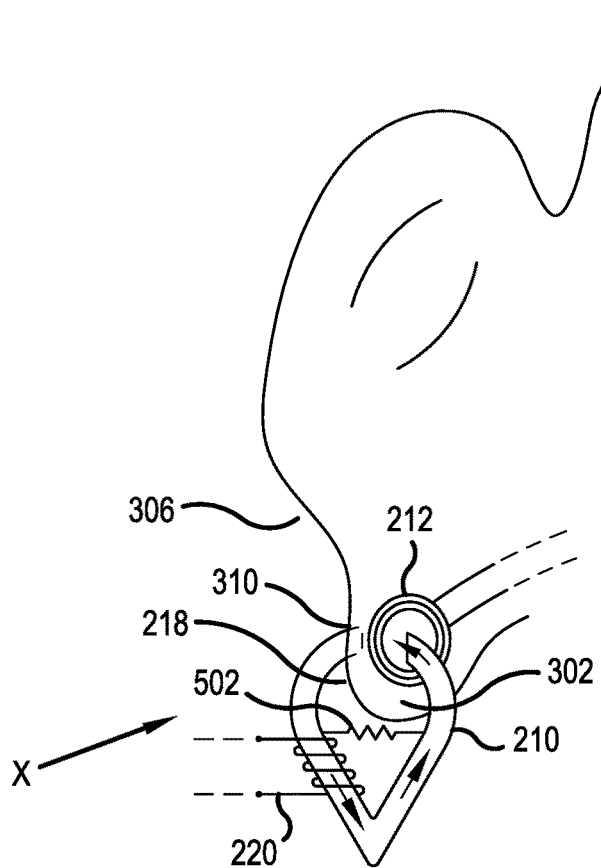
FIG. 6A illustrates an open loop structure attached to a body part according to an embodiment of the disclosure.

FIG. 6A illustrates an open loop structure attached to a body part according to an embodiment of the disclosure. The open loop structure comprises a transmitter coil 220 wound around the loop structure. The fixation unit includes a spring 502 providing a pulling compressive retention force (similar to embodiment disclosed in FIG. 5A). The hollow section 218 is adapted to position a part 302 of the body part 310. When the transmitter coil 220 is excited, a substantial part of the generated magnetic field lines (represented by anti-clockwise arrows) pass through the implantable receiver coil 212. The implementation in FIG. 6A is similar to the one disclosed earlier in FIG. 3 except FIG. 6A utilizes an open loop structure as opposed to the closed loop structure of FIG. 3. In this embodiment, there might be some leakage of the magnetic field lines because of sandwiched skin and body tissue between the two ends (FIG. 6B, 602, 604) of the loop structure 210 instead of a continuous loop structure as disclosed in FIG. 3 that illustrates positioning of the closed loop structure. Nonetheless, the skilled person would appreciate that despite some leakage, a substantial amount of magnetic field lines generated in response to excitation of the transmitter coil would still follow the path of the imaginary line because of the short distance between first end and the second end of the loop structure, in particular, when an implantable magnetic core (FIG. 8, 814) is configured to be positioned within the area enclosed by the perimeter of the implantable receiver coil.

Figure 6B:
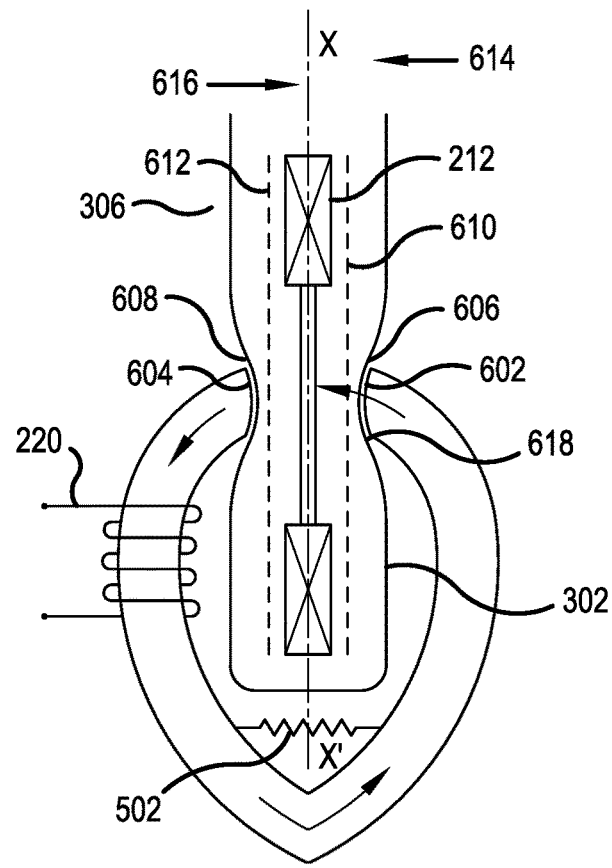
FIG. 6B illustrates an open loop structure attached to a body part according to an embodiment of the disclosure.

FIG. 6B illustrates an open loop structure attached to a body part according to an embodiment of the disclosure. This figure provides a closer illustration of the retention mechanism of the disclosure of FIG. 6A. The loop structure comprises an openable open loop structure comprising a slit (generally defined by the distance D, see FIG. 5) having a first slit end 602 configured to abut a first skin surface 606 of the user and a second slit end 604, opposite to the first slit end 602, configured to abut a second skin surface 608 of the user, the first skin surface 606 and the second skin surface 608 being separated by a body tissue 618.

In an embodiment, the first slit end 602 is adapted to face a first planar side 610 of the implantable receiver coil 212; and a second slit end 604 that is adapted to face a second planar side 612, opposite to the first planar side 610, of the implantable receiver coil 212.

The fixation unit (spring 502) arranged between the inner surface of opposite arms of the loop structure may be adapted to provide a pulling force between the two arms such that a compressive retention force (as represented by compressed skin and body tissue) between the first end 602 and second end 604 is provided to attach the loop structure 210 to the body.

In view of any one of the FIGS. 3 and 6A, it is evident that the transmitter coil 220 and the implantable receiver coil 212 are arranged relative to each other such that the coupling coefficient between the transmitter coil 220 and the implantable receiver coil 212 is independent of orientation of the transmitter coil 220 with respect to the implantable receiver coil 212. The coupling coefficient thus depends upon the arrangement of the loop structure 210 with respect to the implantable receiver coil 212. This arrangement may include interlocked hopf configuration between the loop structure 210 and implantable receiver coil 212.

In another embodiment, planar area (along plane 610 or 612) of the implantable receiver coil 212 is at least same as the cross sectional area (as seen from X-X' in the direction of 614 and/or 616) of the loop structure 210 at an interface (604 or 602) of the loop structure.

Figure 7:
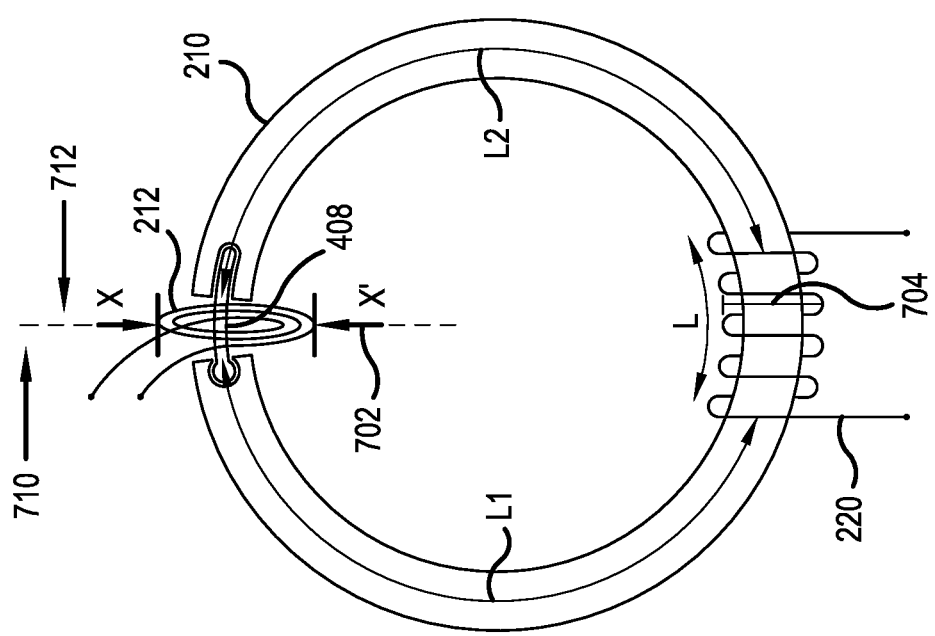
FIG. 7 illustrates arrangement of the transmitter coil and the loop structure with respect to the receiver coil according to an embodiment of the structure.

FIG. 7 illustrates arrangement of the transmitter coil and the loop structure with respect to the receiver coil according to an embodiment of the structure. In an embodiment, the lengthwise distance L1 and/or L2 between the transmitter coil 220 and receiver coil 212 is more than diameter of the receiver coil 702. Additionally, or alternatively, the lengthwise distance L1 and/or L2 between the transmitter coil 220 and receiver coil 212 is more than diameter 704 of the transmitter coil 220. L represents the at least part of length of the loop structure around which the transmitter coil is wound.

In another embodiment, diametric dimensions 702 of the implantable receiver coil 212 is at least same as width of the loop structure. The width refers to cross-sectional thickness of the loop structure as seen from X-X' in the direction of 710 and/or 712. In another embodiment, planar area (along plane 802, FIG. 8) of the implantable receiver coil 212 is at least same as the cross sectional area (as seen from X-X' in the direction of 710 and/or 712) of the loop structure 210 at an interface of the loop structure. The cross sectional area of the loop structure 210 at the interface of the loop structure may include i) cross sectional area at the first end (FIG. 6B, 602) and/or the second end (FIG. 6B, 604) of the loop structure, or ii) cross sectional area of the section (408 or FIG. 4C, 416) of the loop structure that penetrates through the body part at least at one point of the body part.

Figure 8:
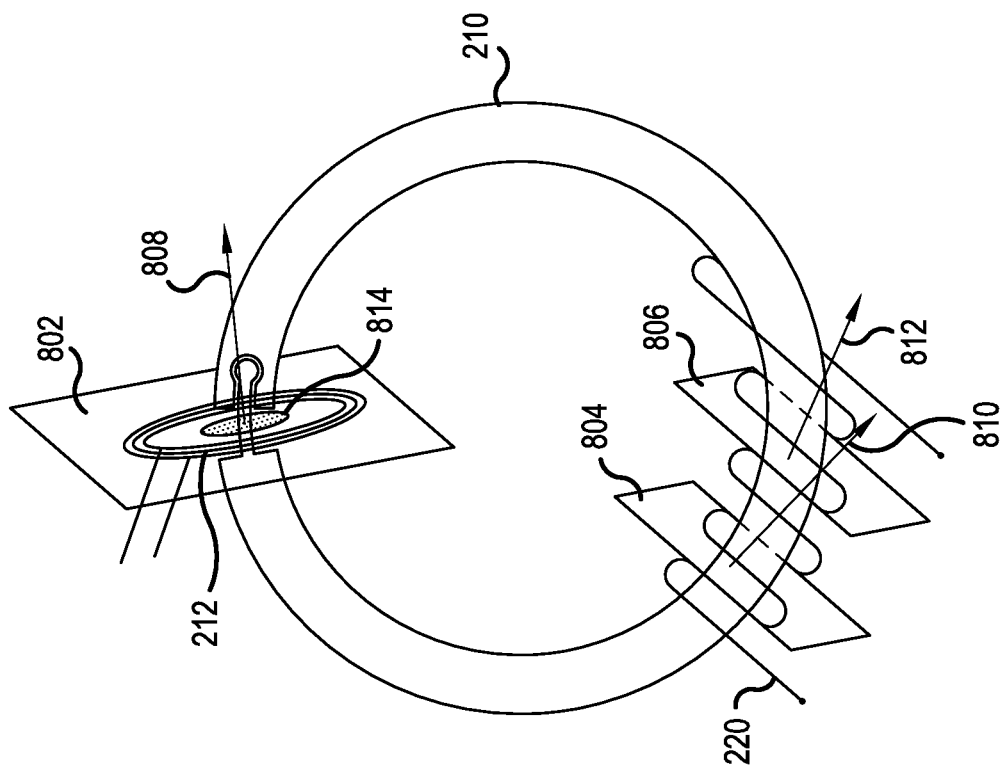
FIG. 8 illustrates a magnetic core positioned within the implantable receiver coil according to an embodiment of the disclosure.

FIG. 8 illustrates a magnetic core positioned within the implantable receiver coil according to an embodiment of the disclosure. In an embodiment, at least one turn of the transmitter coil is non-parallel to the implantable receiver coil, as illustrated by planes 804 and 806 being non-parallel to 802. Additionally, or alternatively, at least one turn of the transmitter coil is non-coaxial with the receiver coil, as illustrated by axis 810 and 812 being non-coaxial with 808. In an embodiment, the implantable receiver coil 212 is in a first plane 802 and the loop structure is along a second plane (parallel to the surface of paper). The first plane 802 and the second plane being at least substantially perpendicular to each other.

In another embodiment, the implantable unit comprises an implantable magnetic core 814 that is configured to be positioned within an area enclosed by a perimeter of the implantable receiver coil 212. The magnetic core is adapted to direct the magnetic field lines to pass through the implantable receiver coil, thus further improving the coupling coefficient between the transmitter coil and receiver coil.

In view of any one of the FIGS. 2, 3, 6 through 8, it is evident that the fixation unit 214 is configured to attach the loop structure 210 around the body part (FIGS. 3, 6A, 310) such that the loop structure 210 and the implantable receiver coil 212 are arranged in an interlocked hopf link configuration.

In view of any one of the FIGS. 2, 3, 6 through 8, it is evident that the fixation unit 214 is configured to attach the loop structure 210 around the body part (FIG. 3, 6 310) such that i) the loop structure 210 and the implantable receiver coil 212 are arranged in an interlocked first hopf link configuration, and ii) the loop structure 210 and the transmitter coil 220 arc arranged in an interlocked second hopf link configuration.

In an embodiment, the fixation unit 214 is selected from a group consisting of a non-magnetic fixation unit (FIGS. 4A through 4E and FIGS. 5A through 5D) and a fixation mechanism that is adapted to attach the loop structure to a user's body independent of any cooperation (interaction) with the implantable unit (FIGS. 4 and 5).

In an embodiment, the fixation unit is selected from a group consisting of a clamp mechanism (FIGS. 4E. 5B, 5D), spring mechanism (FIG. 5A), piercing pin mechanism (FIGS. 4A, 4B, 4C, 4D, 4E), snap-coupling mechanism between the first sub-structure and second sub-structure (FIGS. 4C, 4D, 5D), a magnetic coupling mechanism between the first sub-structure and second sub-structure, and a combination thereof (FIG. 5D).

In an embodiment, the processing unit is configured to process the received data signal and generate an output. The output is configured to generate perceivable stimulation for the user. For example, such perceivable stimulation includes perception of sound in case of implantable hearing aids. The medical device thus may be selected from a group consisting of one or more of i) an implantable hearing aid comprising a cochlear implant comprising an implantable electrode array configured to be positioned within a cochlea of the user, the electrode array being configured to deliver electrical charges in accordance with the output. A typical, non-limiting, description of such cochlear implant is available in pending European patent application EP3045204 (A cochlear implant and an operating method thereof), in particular in FIG. 1B of the referred application where numeral 160 (signal processor) of the referred application illustrates the disclosed electronic unit (FIG. 2, 204), numeral 155 (pulse generator) of the referred application illustrates at least a part of the disclosed implantable processing unit (FIG. 2, 206) and numeral 9 (electrode array) of the referred application illustrates the disclosed electrode array (FIG. 2, 208). The referred application is incorporated herein by reference.

ii) an implantable hearing aid comprising an auditory transmodiolar implant comprising an implantable electrode array configured to be positioned within a modiolus of the user, the electrode array being configured to deliver electrical charges in accordance with the output. A typical, non-limiting, description of the disclosed electronic unit (FIG. 2, 204) and at least a part of the disclosed implantable processing unit (FIG. 2, 206) that may be used in such auditory transmodiolar implant is available in FIG. 1B of pending European patent application EP3045204 (A cochlear implant and an operating method thereof) by numeral 160 (signal processor) and numeral 155 (pulse generator) respectively of the referred application. The implantable electrode array (FIG. 2, 208) that is specifically adapted for auditory transmodiolar implant is disclosed in FIG. 2 of the pending European patent application EP3017843 (Transmodiolar electrode array and a manufacturing method). The referred applications are incorporated herein by reference.

iii) an implantable hearing aid comprising an auditory brainstem implant comprising an implantable electrode array (typically provided as a pad) configured to be implanted directly onto brainstem, the electrode array being configured to deliver the electrical charges in accordance with the output. A typical, non-limiting, description of such auditory brainstem implant is provided in the granted patent U.S. Pat. No. 8,874,238 (Conformal Electrode pad for a stimulating medical device) and in particular in FIG. 1B where numeral 126 (speech processing unit) of the referred patent illustrates the disclosed electronic unit (FIG. 2, 204), numeral 134 (stimulator) of the referred patent illustrates at least a part of the disclosed implantable processing unit (FIG. 2, 206), and numeral 140 (electrode pad) of the referred patent illustrates the disclosed electrode array (FIG. 2, 208). The referred patent is incorporated herein by reference.

iv) an implantable hearing aid comprising a bone conduction hearing aid comprising an implantable vibrator configured to be attached to skull of the user, the vibrator being configured to generate vibrations in accordance with the output. A typical, non-limiting, description of such implantable hearing aid is provided in granted European patent EP1972179 (Hearing aid system) illustrating an implantable vibrator unit (FIG. 1, 106) that illustrate the disclosed vibrator (FIG. 2, 208). A typical, non-limiting, description of such implantable hearing aid is also provided in granted U.S. Pat. No. 9,554,222 (Electromechanical transducer with mechanical advantage) where external speech processing unit (FIG. 2B, 100) illustrates the disclosed electronic unit (FIG. 2, 204), bone conduction transducer (FIG. 2B, 200) illustrates the disclosed implantable processing unit (FIG. 2, 206) and vibrator (FIG. 2. 208). The referred patent is incorporated herein by reference.

v) an implantable hearing aid comprising a middle ear implant comprising a vibratory unit configured to attach to one of the bones of the middle ear and/or to one of the windows of the cochlea, the vibratory unit being configured to generate vibrations in accordance with the output. A typical, non-limiting, description of such middle ear implant is provided in withdrawn European patent application EP2129428 (Implantable auditory stimulation systems having a transducer and a transduction medium) where the audio processor of the referred application in FIGS. 3 and 4 represents the disclosed electronic unit (FIG. 2. 204), demodulation electronics of the referred application in FIGS. 3 and 4 illustrates at least a part of the disclosed implantable processing unit (FIG. 2, 206), and EMT with transduction medium (FIG. 2) or plunger type transducer (FIG. 3) of the referred application illustrates the vibratory unit (FIG. 2, 208). The referred application is incorporated herein by reference.

vi) an artificial pacemaker comprising an electrode array configured to deliver electrical charges in accordance with the output. A typical, non-limiting, description of such artificial pacemaker is provided in granted European patent EP2376193 (Shunt-current reduction techniques for an implantable therapy system) which illustrates an implantable cardiac device (FIG. 1, 16) that illustrates a part of the implantable processing device (FIG. 2, 206) and electrodes (FIG. 7A, 124) illustrating disclosed electrode array (FIG. 2, 208). The referred patent is incorporated herein by reference.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant device comprising
an external unit configured to be worn proximate to a user's ear, the external unit comprising
an electronic unit operationally coupled to a transmitter coil that is configured transmit power and/or data signal over a wireless transcutaneous link,
a coil unit comprising a loop structure with the transmitter coil being wound around and along at least a part of length of the loop structure,
a fixation unit configured to attach the loop structure to the user's ear i) proximal to a loop-shaped implantable receiver coil that is configured to be implanted within the ear, and ii) around the ear of the user such that a part of the ear is positioned in a hollow section of the loop structure; and
an implantable unit comprising
the implantable receiver coil configured to receive the power and/or data signal over the wireless transcutaneous link,
a processing unit configured to i) process the received data signal to control functionalities of at least one of the components of the implantable unit, and/or ii) utilize the received power for operation of at least one of the components of the implantable unit, and
an electrode array configured to be inserted into a cochlea of the user, wherein
the wireless transcutaneous link comprises a coupling between the transmitter coil and the receiver coil, and
when the loop structure is attached using the fixation unit such that at least a substantial number of magnetic field lines generated in response to excitation of the transmitter coil passes through the opening in the loop-shaped implantable receiver coil.

2. The cochlear implant device according to claim 1, wherein the fixation unit is adapted to attach the loop structure with respect to the implantable receiver coil in an arrangement such that one section of the implantable receiver coil is positioned within the hollow section of the loop structure whereas the other section of the implantable receiver coil is positioned outside the hollow section of the loop structure.

3. The cochlear implant device according to claim 1, wherein the fixation unit is configured to attach the loop structure proximal to the implantable receiver coil such that the loop structure passes through the implantable receiver coil and the implantable receiver coil winds around a segment of the loop structure.

4. The cochlear implant device according to claim 1, wherein the fixation unit is configured to attach the loop structure around the ear such that the loop structure and the implantable receiver coil are arranged in an interlocked hopf link configuration.

5. The cochlear implant device according to claim 1, wherein the loop structure comprises an openable closed loop structure comprising a section that is configured to penetrate through the body part at least at one point of the body part.

6. The cochlear implant device according to claim 1, wherein the loop structure comprises an openable open loop structure comprising a slit having a first slit end configured to abut a first skin surface of the user and a second slit end, opposite to the first slit end, configured to abut a second skin surface of the user, the first skin surface and the second skin surface being separated by a body tissue.

7. The cochlear implant device according to claim 6, wherein the first slit end is adapted to face a first planar side of the implantable receiver coil; and a second slit end is adapted to face a second planar side, opposite to the first planar side, of the implantable receiver coil.

8. The cochlear implant device according to claim 1, wherein planar area of the implantable receiver coil is at least same as cross sectional area of the loop structure at an interface of the loop structure.

9. The cochlear implant device according to claim 1, wherein the implantable unit comprises an implantable magnetic core that is configured to be positioned within an area enclosed by a perimeter of the implantable receiver coil.

10. The cochlear implant device according to claim 1, wherein the at least substantial number of magnetic field lines generated in response to excitation of the transmitter coil are generated within the loop structure.

11. The cochlear implant device according to claim 1, wherein at least one turn of the transmitter coil is non-parallel to the implantable receiver coil.

12. The cochlear implant device according to claim 1, wherein the loop structure comprises a first sub-structure and a second sub-structure, the first sub-structure and a second sub-structure being configured to operationally connect with each other to form the openable closed loop structure or openable open loop structure.

13. The cochlear implant device according to claim 1, wherein the fixation unit is selected from a group consisting of a non-magnetic fixation unit and a fixation mechanism that is adapted to attach the loop structure to a user's ear independent of any cooperation with the implantable unit.

14. The cochlear implant device according to claim 1, wherein the fixation unit is selected from a group consisting of a clamp mechanism, spring mechanism, piercing pin mechanism, snap-coupling mechanism between the first sub-structure and second sub-structure, a magnetic coupling mechanism between the first sub-structure and second sub-structure, and a combination thereof.

15. The cochlear implant device according to claim 1, wherein the processing unit is configured to process the received data signal and generate an output, and the electrode array is configured to deliver electrical charges in accordance with the output.

16. The cochlear implant device according to claim 2, wherein the fixation unit is configured to attach the loop structure proximal to the implantable receiver coil such that a loop axis or an extrapolated loop axis of the loop structure passes through the implantable receiver coil.

17. The cochlear implant device according to claim 2, wherein the fixation unit is configured to attach the loop structure around the body part such that the loop structure and the implantable receiver coil are arranged in an interlocked hopf link configuration.

18. The cochlear implant device according to claim 3, wherein the fixation unit is configured to attach the loop structure around the body part such that the loop structure and the implantable receiver coil are arranged in an interlocked hopf link configuration.

19. The cochlear implant device according to claim 2, wherein the loop structure comprises an openable closed loop structure comprising a section that is configured to penetrate through the body part at least at one point of the body part.

20. The cochlear implant device according to claim 3, wherein the loop structure comprises an openable closed loop structure comprising a section that is configured to penetrate through the body part at least at one point of the body part.

* * * * *